(12) United States Patent
Tamura et al.

US010807073B2

(10) Patent No.: US 10,807,073 B2
(45) Date of Patent: Oct. 20, 2020

(54) METHOD FOR PRODUCING CATALYST, AND METHOD FOR PRODUCING UNSATURATED NITRILE

(71) Applicant: ASAHI KASEI KABUSHIKI KAISHA, Tokyo (JP)

(72) Inventors: Sho Tamura, Tokyo (JP); Dai Nagata, Tokyo (JP)

(73) Assignee: ASAHI KASEI KABUSHIKI KAISHA, Tokyo ( * ) Notice: Subject to any disclaimer, the term of this patent is extended or adjusted under 35 U.S.C. 154(b) by 405 days.

(21) Appl. No.: 15/561,441

(22) PCT Filed: Mar. 24, 2016

(86) PCT No.: PCT/JP2016/059342
§ 371 (c)(1),
(2) Date: Sep. 25, 2017

(87) PCT Pub. No.: WO2016/152964
PCT Pub. Date: Sep. 29, 2016

(65) Prior Publication Data
US 2018/0117565 A1  May 3, 2018

(30) Foreign Application Priority Data

Mar. 26, 2015 (JP) .................. 2015-065054
May 15, 2015 (JP) .................. 2015-100183
Aug. 4, 2015 (JP) .................. 2015-154467

(51) Int. Cl.
*B01J 23/28* (2006.01)
*B01J 37/04* (2006.01)
*B01J 23/30* (2006.01)
*B01J 27/057* (2006.01)
*B01J 37/02* (2006.01)
*C07C 253/24* (2006.01)
*C07C 255/08* (2006.01)
*B01J 37/00* (2006.01)
*B01J 23/00* (2006.01)
*C07B 61/00* (2006.01)

(52) U.S. Cl.
CPC .............. *B01J 23/28* (2013.01); *B01J 23/002* (2013.01); *B01J 23/30* (2013.01); *B01J 27/057* (2013.01); *B01J 37/0045* (2013.01); *B01J 37/02* (2013.01); *B01J 37/0207* (2013.01); *B01J 37/04* (2013.01); *C07C 253/24* (2013.01); *C07C 255/08* (2013.01); *C07B 61/00* (2013.01)

(58) Field of Classification Search
CPC . B01J 23/002; B01J 23/28; B01J 23/30; B01J 27/057; B01J 37/0045; B01J 37/02; B01J 37/0207; B01J 37/04; C07B 61/00; C07C 253/24; C07C 255/08
See application file for complete search history.

(56) References Cited

U.S. PATENT DOCUMENTS

| 5,622,908 A | 4/1997 | Abel et al. |
| 2010/0240921 A1* | 9/2010 | Tateno ................ B01J 23/002 558/308 |
| 2013/0053596 A1 | 2/2013 | Kato et al. |
| 2013/0225862 A1 | 8/2013 | Tateno et al. |
| 2013/0253217 A1* | 9/2013 | Ishii .................... B01J 23/002 558/319 |
| 2015/0105583 A1 | 4/2015 | Sakai et al. |

FOREIGN PATENT DOCUMENTS

| CN | 101405079 A | 4/2009 |
| JP | 7-144131 A | 6/1995 |
| JP | 7-185354 A | 7/1995 |
| JP | 10-28862 A | 2/1998 |
| JP | 2001-72641 A | 3/2001 |
| JP | 3769866 B2 | 2/2006 |

(Continued)

OTHER PUBLICATIONS

Supplementary European Search Report dated Feb. 21, 2018, in European Patent Application No. 16768867.0.
International Preliminary Report on Patentability and Written Opinion dated Oct. 5, 2017, in PCT International Application No. PCT/JP2016/059342.
International Search Report dated Jun. 21, 2016, in PCT International Application No. PCT/JP2016/059342.

*Primary Examiner* — Amber R Orlando
*Assistant Examiner* — Syed T Iqbal
(74) *Attorney, Agent, or Firm* — Birch, Stewart, Kolasch & Birch, LLP.

(57) ABSTRACT

The present invention provides a method for producing a catalyst to be used for a gas-phase catalytic ammoxidation reaction of propane, the method comprising a preparation step of dissolving or dispersing a raw material to thereby obtain a prepared raw material liquid, a first drying step of drying the prepared raw material liquid to thereby obtain a dried material, a calcination step of calcining the dried material to thereby obtain a composite oxide having a predetermined composition, an impregnation step of impregnating the composite oxide with a solution containing at least one specific element selected from the group consisting of tungsten, molybdenum, tellurium, niobium, vanadium, boron, bismuth, manganese, iron, antimony, phosphorus and rare earth elements to thereby obtain an impregnated composite oxide, and a second drying step of drying the impregnated composite oxide, wherein at least one of the impregnation step o and the second drying step is a step of impregnating the composite oxide or drying the impregnated composite oxide while stirring by a specific stirring power.

8 Claims, No Drawings

(56) References Cited

FOREIGN PATENT DOCUMENTS

| | | |
|---|---|---|
| JP | 2007-117818 A | 5/2007 |
| JP | 5190994 B2 | 2/2013 |
| WO | WO 2011/142178 A1 | 11/2011 |
| WO | WO 2013/172414 A1 | 11/2013 |

* cited by examiner

METHOD FOR PRODUCING CATALYST, AND METHOD FOR PRODUCING UNSATURATED NITRILE

TECHNICAL FIELD

The present invention relates to a method for producing a catalyst, and a method for producing an unsaturated nitrile.

BACKGROUND ART

Conventionally, a method for producing unsaturated nitriles by an ammoxidation reaction, which is one of gas-phase catalytic oxidation reactions, using olefins such as propylene as a raw material has been known. In recent years, however, attention has been paid on a method for producing an unsaturated nitrile of acrylonitrile by an ammoxidation reaction using propane in place of olefins such as propylene as a raw material. As a catalyst to be used for the gas-phase catalytic ammoxidation reaction of propane, a catalyst obtained by mixing and calcining molybdenum, vanadium and the like is used, and a technique of carrying out a post-treatment on the calcined catalyst according to needs has also been studied.

For example, Patent Literature 1 discloses a technique of immersing a Mo—V—Sb—Nb-based catalyst in a solution containing tungsten and manganese. Further Patent Literature 2 discloses a technique of impregnating a Mo—V—Sb/Te-based catalyst with a solution containing one or more elements selected from the group consisting of tungsten, molybdenum, chromium, zirconium, titanium, niobium, tantalum, vanadium, bismuth, tellurium, palladium, cobalt, nickel, iron, phosphorus, rare earth elements, alkali metals and alkaline earth metals. Further Patent Literature 3 discloses a technique of immersing a Mo—V—Sb—Nb—W-based catalyst in a solution containing tungsten.

CITATION LIST

Patent Literature

Patent Literature 1: Japanese Patent No. 5190994
Patent Literature 2: Japanese Patent No. 3769866
Patent Literature 3: International Publication No. WO2011/142178

SUMMARY OF INVENTION

Technical Problem

In the case where an unsaturated nitrile is industrially produced by a gas-phase catalytic ammoxidation reaction of propane, the amount of a catalyst to be used in the reaction is required to be at least several hundred kilograms. Since the amount of a catalyst required exceeds several hundred tons not in a small number of cases, a large amount of the catalyst is required to be produced.

At least according to the catalyst production methods described in the above Patent Literatures 1 to 3, however, in the case where a large amount of the catalyst is produced, when a composite oxide being a raw material of the catalyst is impregnated with or immersed in a solution containing specific elements, the yields of unsaturated nitriles produced by using the catalysts produced cannot be sufficiently raised because breakage is generated in the catalyst produced, unevenness is caused in drying of the catalyst; and the dispersibility of the specific elements into the composite oxide becomes poor.

Then, the present invention has an object to provide a method for producing a catalyst to be used for a gas-phase catalytic ammoxidation reaction of propane, the method being capable of providing an unsaturated nitrile in a high yield from propane and being capable of producing the catalyst in a large amount.

Solution to Problem

As a result of exhaustive studies to solve the above problems in conventional technologies, the present inventors have found that by using a method for producing a catalyst comprising a specific preparation step, a specific first drying step, a specific calcination step, a specific impregnation step and a specific second drying step, the catalyst capable of providing an unsaturated nitrile in a high yield from propane can be produced in a large amount; and this finding has led to the completion of the present invention.

That is, the present invention is as follows.

[1] A method for producing a catalyst to be used for a gas-phase catalytic ammoxidation reaction of propane, the method comprising:

a preparation step of dissolving or dispersing a raw material to thereby obtain a prepared raw material liquid;

a first drying step of drying the prepared raw material liquid to thereby obtain a dried material;

a calcination step of calcining the dried material to thereby obtain a composite oxide represented by following formula (1);

an impregnation step of impregnating the composite oxide with a solution containing at least one specific element selected from the group consisting of tungsten, molybdenum, tellurium, niobium, vanadium, boron, bismuth, manganese, iron, antimony, phosphorus and rare earth elements to thereby obtain an impregnated composite oxide; and a second drying step of drying the impregnated composite oxide, wherein at least one of the impregnation step and the second drying step a step of impregnating the composite oxide or drying the impregnated composite oxide while stirring by a stirring power per unit composite oxide volume given by following formula (2):

$$Mo_1V_aNb_bA_cX_dZ_eO_n \quad (1)$$

wherein A represents at least one element selected from the group consisting of Sb and Te; X represents at least one element selected from the group consisting of W, Bi, Mn and Ti; and Z represents at least one element selected from the group consisting of La, Ce, Pr, Yb, Y, Sc, Sr and Ba; and a, b, c, d, e and n represent elemental ratios of the respective elements per one element of Mo and $0.01 \leq a \leq 1.00$, $0.01 \leq b \leq 1.00$, $0.01 \leq c \leq 1.00$, $0.00 \leq d \leq 1.00$ and $0.00 \leq e \leq 1.00$, and n is a value determined by the atomic valences of the constituent elements of the composite oxide;

$$Pv\ (kW/m^3) = P\ (kW)/V\ (m^3) \quad (2)$$

wherein Pv represents a stirring power per unit composite oxide volume ($kW/m^3$); P represents an electric power (kW) used in a stirring time; and V represents a volume ($m^3$) of the composite oxide packed in a stirring apparatus; and Pv is $0.001 \leq Pv \leq 300$.

[2] The method for producing the catalyst according to [1], wherein in the second drying step, the drying is carried out at a drying rate of 0.5% by mass/hr or higher and 20% by mass/hr or lower while the composite oxide is being fluidized.

[3] The method for producing a catalyst according to [1] or [2], wherein in the catalyst, an elemental ratio of the specific element to molybdenum in the composite oxide is 0.0001 or higher and 0.50 or lower.

[4] The method for producing the catalyst according to any of [1] to [3], wherein in the second drying step, a pressure in an apparatus is 20 kPa or higher and 110 kPa or lower in absolute pressure.

[5] The method for producing the catalyst according to any of [1] to [4], wherein in the second drying step, a drying time is 0.5 hour or longer and 50 hours or shorter.

[6] The method for producing a catalyst according to any of [1] to [5], wherein in the second drying step, the composite oxide has a temperature of 30° C. or higher and 650° C. or lower.

[7] The method for producing the catalyst according to any of [1] to [6], wherein in the impregnation step, an amount of a solution comprising the specific element is 0.1 time or larger and 3.0 times or smaller based on a pore volume of the composite oxide.

[8] A method for producing an unsaturated nitrile by a gas-phase catalytic ammoxidation reaction of propane, the method comprising a contact step of bringing a catalyst obtained by the method for producing the catalyst according to any of [1] to [7] into contact with propane.

Advantageous Effect of Invention

According to the method for producing a catalyst according to the present invention, the catalyst capable of providing an unsaturated nitrile in a high yield from propane can be produced in a large amount.

DESCRIPTION OF EMBODIMENT

Hereinafter, an embodiment to carry out the present invention (hereinafter, referred to simply as "the present embodiment") will be described in detail. The following present embodiment is an exemplification to describe the present invention, and has no tenor of limiting the present invention to the following contents. The present invention can be carried out by being variously changed and modified within its gist.

[Method for Producing a Catalyst]

A method for producing a catalyst of the present embodiment is a method for producing a catalyst to be used for a gas-phase catalytic ammoxidation reaction of propane, and comprises a preparation step of dissolving or dispersing a raw material to thereby obtain a prepared raw material liquid (hereinafter, referred to also as "step (1)"), a first drying step of drying the prepared raw material liquid to thereby obtain a dried material (hereinafter, referred to also as "step (2)"), a calcination step of calcining the dried material to thereby obtain a composite oxide represented by the following formula (1) (hereinafter, referred to also as step (3)"), an impregnation step of impregnating the composite oxide with a solution (hereinafter, referred to simply as "impregnating solution") containing at least one specific element selected from the group consisting of tungsten, molybdenum, tellurium, niobium, vanadium, boron, bismuth, manganese, iron, antimony, phosphorus and rare earth elements to thereby obtain an impregnated composite oxide (hereinafter, referred to also as "step (4)"), and a second drying step of drying the impregnated composite oxide (hereinafter, referred to also as "step (5)"). Further at least one of the impregnation step and the second drying step is a step of impregnating the composite oxide or drying the impregnated composite oxide while stirring by a stirring power per unit composite oxide volume given by the following formula (2). Here, the "raw material" is not especially limited as long as being a compound containing constituent elements of the catalyst, but specifically, compounds described later can be used.

$$Mo_1V_aNb_bA_cX_dZ_eO_n \quad (1)$$

In the formula (1), A represents at least one element selected from the group consisting of Sb and Te; X represents at least one element selected from the group consisting of W, Bi, Mn and Ti; and Z represents at least one element selected from the group consisting of La, Ce, Pr, Yb, Y, Sc, Sr and Ba. a, b, c, d, e and n represent elemental ratios of the respective elements per one element of Mo and $0.01 \leq a \leq 1.00$, $0.01 \leq b \leq 1.00$, $0.01 \leq c \leq 1.00$, $0.00 \leq d \leq 1.00$ and $0.00 \leq e \leq 1.00$ and n is a value determined by the atomic valences of the constituent elements of the composite oxide.

$$Pv \, (kW/m^3) = P \, (kW)/V \, (m^3) \quad (2)$$

In the formula (2), Pv represents a stirring power ($kW/m^3$) per unit composite oxide volume; P represents an electric power (kW) used in the stirring time; and V represents a volume ($m^3$) of the composite oxide packed in a stirring apparatus. P is $0.001 \leq Pv \leq 300$.

In the formula (1), a representing the elemental ratio of V per one element of Mo is $0.05 \leq a \leq 1.00$, preferably $0.075 \leq a \leq 0.70$, and more preferably $0.10 \leq a \leq 0.40$. When a is in the above range, a more proper propane activity can be attained and the decomposition of acrylonitrile is more suppressed. Then, b representing the elemental ratio of Nb per one element of Mo is $0.01 \leq b \leq 1.00$, preferably $0.02 \leq b \leq 0.70$, and more preferably $0.03 \leq b \leq 0.40$. When b is in the above range, a more proper propane activity can be attained and the decomposition of acrylonitrile is more suppressed. Further, c representing the elemental ratio of A per one element of Mo is $0.01 \leq c \leq 1.00$, preferably $0.03 \leq c \leq 0.80$, and more preferably $0.05 \leq c \leq 0.50$. When c is in the above range, the ammoxidation reaction more easily advances. Further, a/c representing an elemental ratio of V to A is preferably $0.50 \leq (a/c) \leq 2.00$, more preferably $0.60 \leq (a/c) \leq 1.80$, and still more preferably $0.70 \leq (a/c) \leq 1.60$. When a/c is in the above range, the decomposition of acrylonitrile produced tends to be more suppressed. A represents at least one element selected from the group consisting of Sb and Te.

In the formula (1), d representing the elemental ratio of X per one element of Mo is $0.00 \leq d \leq 1.00$, preferably $0.001 \leq d \leq 0.50$, more preferably $0.003 \leq d \leq 0.40$, and still more preferably $0.005 \leq d \leq 0.30$. When d is in the above range, the decomposition activity of acrylonitrile is more suppressed, and a more proper propane activity can be attained. X represents at least one element selected from the group consisting of W, B Mn and Ti, and from the viewpoint of the industrial long-term use, X represents preferably an element of W, Bi or Mn, and since the decomposition of acrylonitrile tends to be suppressed, more preferably an element of W.

In the formula (1), e representing the elemental ratio of Z per one element of Mo is $0.00 \leq e \leq 1.00$, preferably $0.0001 \leq e \leq 0.50$, and more preferably $0.0005 \leq e \leq 0.30$. When e is in the above range, the decomposition of acrylonitrile and the combustion of ammonia are suppressed. Z represents at least one element selected from the group consisting of La, Ce, Pr, Yb, Y, Sc, Sr and Ba.

A carrier carrying the catalyst of the present embodiment preferably contains silica. In the case where the catalyst is carried by the carrier containing silica, since the catalyst tends to have a high mechanical strength, the catalyst can suitably be used for a gas-phase catalytic ammoxidation reaction using a fluidized-bed reactor described later. In the case where the carrier contains silica, the content of silica in the carrier is, based on the total mass (100% by mass) of the catalyst and the carrier, in terms of $SiO_2$, preferably 20% by mass or higher and 70% by mass or lower, more preferably 25% by mass or higher and 65% by mass or lower, and still more preferably 30% by mass or higher and 60% by mass or lower. The content of silica is, from the viewpoint of the strength and the powdering prevention, preferably 20% by mass or higher. The content of silica of 20% by mass or higher tends to allow stable operation of the catalyst its industrial use, and to make the loss of the carried catalyst very little, and the case is preferable also economically. Further from the viewpoint of providing a sufficient activity and making the amount of the necessary catalyst proper, the content of silica is preferably 70% by mass or lower. Particularly in the case where the catalyst is used for a fluidized-bed reaction, when the content of silica is 70% by mass or lower, the specific gravity of the catalyst is suitable and the catalyst tends to easily make a good fluid state.

[Step (1): Preparation Step]

The step (1) of the present embodiment dissolves or disperses a raw material to obtain a prepared raw material liquid. The raw material to be used at this time is not especially limited as long as being capable of providing a composite oxide having a predetermined composition to be obtained in the step (2) described later, but examples thereof include a raw material of Mo, a raw material of V, a raw material of Nb, raw material of A, a raw material of X and a raw material of Z.

Examples of a method for dissolving or dispersing the raw material include, though not limited to the following, a method of dissolving or dispersing in water, and a method of dissolving or dispersing in a solvent, and the method of dissolving or dispersing in water is preferable. Then, the prepared raw material liquid contains, for example, a raw material of Mo, a raw material of V, a raw material of Nb, a raw material of Sb or a raw material of Te, a raw material of X and a raw material of Z whose ratios have been regulated so as to make a composition of a composite oxide represented by the formula (1) obtained by the step (2) described later.

The raw material of Mo and the raw material of V are not especially limited, but ammonium heptamolybdate [$(NH_4)_6Mo_7O_{24}.4H_2O$] and ammonium metavanadate [$NH_4VO_3$] can be used, respectively.

The raw material of Nb is not especially limited, but niobic acid, an inorganic acid salt of niobium and an organic acid salt of niobium can be used suitably. Among these, niobic acid is preferable. Niobic acid is represented by $Nb_2O_5.nH_2O$, and called also a niobium hydroxide or a niobium oxide hydrate. It is also preferable to use, as the raw material of Nb, a mixture of niobic acid and a dicarboxylic acid in which the molar ratio (dicarboxylic acid/niobium) of the dicarboxylic acid to niobium is 1.0 or higher and 4.0 or lower. The dicarboxylic acid in this case is not especially limited, but oxalic acid is preferable.

The raw material of A includes a raw material of Sb and a raw material of Te. The raw material of Sb is not especially limited, but biantimony trioxide [$Sb_2O_3$] is preferable. The raw material of Te is not especially limited, but telluric acid [$Te(OH)_6$] is preferable.

The raw material of X is not especially limited as long as being a substance containing at least one element selected from the group consisting of W, Te, Bi and Mn, and a compound containing these elements and a substance in which the metals of these elements have been solubilized with an adequate reagent can be used. Examples of the compounds containing these elements include salts containing these elements such as ammonium salt, nitrate salt, carboxylate salt, carboxylic acid ammonium salt, peroxocarboxylate salt, peroxocarboxylic acid ammonium salt, haloganated ammonium salt, halide, acetylacetonate and alkoxide. Among these, preferable as the raw material of X are water-soluble raw materials containing these elements such as nitrate salt and carboxylate salt, and more preferable is ammonium metatungstate.

The raw material of Z is not especially limited as long as being a substance containing at least one element selected from the group consisting of La, Ce, Pr, Yb, Y, Sc, Sr and Ba, and a compound containing these elements and a substance in which the metals of these elements have been solubilized with an adequate reagent can be used. Examples of the compounds containing these elements include salts containing these elements such as nitrate salt (for example, cerium nitrate), carboxylate salt, carboxylic acid ammonium salt, peroxocarboxylate salt, peroxocarboxylic acid ammonium salt, haloganated ammonium salt, halide, acetylacetonate and alkoxide. Among these, preferable are water-soluble raw materials containing these elements such as nitrate salt and carboxylate salt.

A raw material of the silica contained in the carrier is not especially limited, and for a part of or the whole of the silica raw material, silica sol and/or powdery silica can also be used. The powdery silica is preferably one produced by a pyrogenetic method. By using the powdery silica previously dispersed in water, addition and mixing to a slurry becomes easy. A dispersing method is not especially limited, and the powdery silica can be dispersed by a common homogenizer, homomixer, ultrasonic vibrator or the like singly or in combination.

[Step (2): First Drying Step]

The step (2) of the present embodiment dries the prepared raw material liquid obtained in the above step (1) to thereby obtain a dried material. By drying the prepared raw material liquid (for example, slurry) obtained through the step (1), the dried material to become a catalyst precursor is obtained. The drying can be carried out by a known method, for example, spray drying or evaporation to dryness. In the case where a fluidized-bed reaction system is employed for the gas-phase catalytic ammoxidation reaction, from the viewpoint of making the flowability in a reactor to be in a favorable state and the like, it is preferable that a microspherical dried material be obtained. In order to obtain the microspherical dried material, spray drying is preferably employed as the drying method. Atomization in the spray drying may be by any of a centrifugal system, a twin fluid nozzle system and a high-pressure nozzle system. A drying heat source to be used for spray drying includes air heated by steam, an electric heater or the like. The inlet port temperature of a drier of an apparatus to be used for spray drying is, from the viewpoint of making the shape and/or strength of composite oxide particles obtained in the step (3) described later to be in a favorable state, improving the performance of the obtained composite oxide, and the like, preferably 150° C. or higher and 300° C. or lower. Further the outlet port temperature of the drier is preferably 100° C. or higher and 160° C. or lower.

The spraying rate, the liquid feed rate of the prepared raw material liquid, the rotation frequency of an atomizer in the case of employing the centrifugal system, and the like may be regulated according to the size of the apparatus and so that the particle diameter of an obtained dried material falls in a suitable range. Specifically, the average particle diameter of the dried material is preferably 5.0 μm or larger and 200 μm or smaller, and more preferably 10 μm or larger and 150 μm or smaller. The average particle diameter of the dried material is determined by measuring the particle size distribution according to JIS R1629-1997 "Determination of particle size distributions for fine ceramic raw powders by laser diffraction method", and averaging the measurement in terms of volume. In more detail, a part of the dried material is calcined in air at 400° C. for 1 hour, and the particle size distribution of particles obtained as a measurement object is measured by using a laser diffraction scattering particle size distribution analyzer (manufactured by Beckman Coulter, Inc., trade name: "LS230"). The reason that the average particle diameter is measured after a part of the dried material "is calcined in air at 400° C. for 1 hour" is to prevent the dried material from being dissolved in water. That is, "being calcined in air at 400° C. for 1 hour" is solely for the measurement, and is irrelevant to the calcination step described later. It is allowed to be regarded that the particle diameter does not nearly change before and after the calcination.

With respect to a method of measuring the average particle diameter of the dried material, more specifically, the measurement of the average particle diameter is carried out as follows according to the manual attached to a laser diffraction scattering particle size distribution analyzer (manufactured by Beckman Coulter, Inc., trade name: "LS230"). First, a background measurement (RunSpeed60) is carried out; and thereafter, 0.2 g of particles is weighed in an adequate-size screw tube and 10 cc of water is added. A lid is put on the screw tube (being closed), which is sufficiently shaken to disperse the particles in water. An ultrasonic wave of 300 W is applied by the analyzer and the screw tube is again sufficiently shaken. Thereafter, the particles dispersed in water are injected in the analyzer body by a syringe so as to have a suitable concentration (concentration 10, PIDS 60) under the application of the ultrasonic wave. When the concentration indication becomes stable, the application of the ultrasonic wave is suspended; the resultant is allowed to stand still for 10 sec; and thereafter, the measurement is initiated (measurement time: 90 sec). The value of a median diameter of the measurement result is defined as an average particle diameter.

For the purpose of preventing deposition of the catalyst precursor in the spray drying apparatus, the spray drying apparatus is preferably equipped with a vibrating machine to impart vibration to the spray drying apparatus or a catalyst precursor deposition-preventive apparatus such as an air knocker to impart impacts thereto. Further it is also preferable that the spray drying be once suspended at a suitable frequency and the apparatus interior be washed with water or the like. The measurement of the above spectrum is preferably carried out right after the step (2) where unintended heating is liable to occur.

The operating condition of the air knocker equipped in the drying apparatus can be adjusted optionally according to the size of the apparatus, the thickness of the wall and the exfoliation condition of deposits. Examples of the operating condition include the impact magnitude and the impact frequency of the air knocker, the increase and decrease of the number of the air knockers installed, and the alteration of its installation position. It is preferable that the impact magnitude of the air knocker be so strong as not to deform and damage the wall surfaces and/or other drying apparatus portions even in a long-term operation. From the similar viewpoint, the impact frequency is preferably one or more times in 1 min, and more preferably one or more times in 10 sec. With respect to the number of the air knockers installed and the installation portions, it is preferable that the number be increased for portions where intense deposits are recognized by the observation of the interior after the long-term operation, knockers on portions where almost no deposits are recognized be transferred to portions where intense deposits are recognized, and the like.

[Step (3): Calcination Step]

The step (3) of the present embodiment is a step of calcining the dried material obtained in the step (2) to thereby obtain a composite oxide represented by the following (1).

$$Mo_1V_aNb_bA_cX_dZ_eO_n \quad (1)$$

In the formula (1), A represents at least one element selected from the group consisting of Sb and Te; X represents at least one element selected from the group consisting of W, Bi, Mn and Ti; and Z represents at least one element selected from the group consisting of La, Ce, Pr, Yb, Y, Sc, Sr and Ba. a, b, c, d, e and n represent elemental ratios of the respective elements per one element of Mo and $0.01 \leq a \leq 1.00$, $0.01 \leq b \leq 1.00$, $0.01 \leq c \leq 1.00$, $0.00 \leq d \leq 1.00$ and $0.00 \leq e \leq 1.00$, and n is a number determined by the atomic valences of the constituent elements of the composite oxide.

As an apparatus for calcination (hereinafter, referred to also as "kiln"), for example, a rotary kiln can be used. The shape of the kiln is not especially limited, but when the shape is tubular (calcining tube), it is preferable from the viewpoint of enabling continuous calcination to be carried out, and particularly being cylindrical is more preferable. A heating system to heat the kiln is preferably an external heating system from the viewpoint of easily regulating the calcination temperature so as to make a favorable temperature-elevation pattern, and the like, and an electric oven can suitably be used. The size and material of the calcining tube can be selected adequately according to the calcination condition and the amount calcinated. The inner diameter of the calcining tube is, from the viewpoint of regulating, at proper values, such a calcination time and a production volume that make no unevenness in the calcination temperature distribution in the composite oxide layer, and the like, preferably 70 mm or larger and 2,000 mm or smaller, and more preferably 100 mm or larger and 1,700 mm or smaller. Further the length of the calcining tube is, from the viewpoint of making the distribution of the residence time, that is, the calcination time of the dried material in the calcining tube to be as narrow as possible, preventing the strain of the calcining tube, regulating the calcination time and the production volume at proper values, and the like, preferably 200 mm or longer and 10,000 mm or shorter, and more preferably 800 mm or longer and 8,000 mm or shorter. In the case where impacts are imparted to the calcining tube, the wall thickness is, from the viewpoint of having such a thickness that the impacts do not damage the calcining tube, preferably 2 mm or larger, and more preferably 4 mm or larger. The wall thickness is, further from the viewpoint that the impacts are transmitted sufficiently into the calcining tube interior, preferably 100 mm or smaller, and more preferably 50 mm or smaller. Further from the viewpoint of regulating, at proper values, such a calcination time and a production volume of the composite oxide that make no unevenness in the calcination temperature distribution and the calcination time distribution in the composite oxide layer, and the like, it is preferable that the calcining tube have a tilt to the direction in which the powder flows, and the height of the outlet port of the powder be made lower than the height of the inlet port of the powder. Further from the similar viewpoint, the angle θ of the tilt from the horizontality is preferably 0°<θ<80°, and more preferably 1°≤θ≤40°.

The material of the kiln is not especially limited preferably as long as having the heat resistance and such a strength that the impacts do not damage the kiln, and for example, SUS can suitably be used.

The calcining tube can also be partitioned into two or more zones by installing, in the calcining tube, a weir plate having a hole to pass the powder through on its center perpendicularly (or nearly perpendicularly) to the flow of the powder. By installing the weir plate, it becomes easy for the residence time of the powder in the calcining tube to be secured. The number of the weir plate may be one or in a plural number. From the viewpoint of making good the durability and the heat resistance to the calcination atmosphere, the material of the weir plate is preferably a metal, and the same material as that of the calcining tube can suitably be used. The height of the weir plate can be adjusted according to the residence time to be secured. For example, in the case where a rotary kiln having a SUS-made calcining tube of 150 mm in inner diameter and 1,150 mm in length is used and the dried material is fed at 250 g/hr, the height of the weir plate is preferably 5.0 mm or higher and 50 mm or lower, more preferably 10 mm or higher and 40 mm or lower, and still more preferably 13 mm or higher and 35 mm or lower. The thickness of the weir plate is not especially limited, and is preferably adjusted according to the size of the calcining tube. For example, in the case of a rotary kiln having a SUS-made calcining tube of 150 mm in inner diameter and 1,150 mm in length, the thickness of the weir plate is preferably 0.3 mm or larger and 30 mm or smaller, and more preferably 0.5 mm or larger and 15 mm or smaller.

In order to prevent breakage, cracking and the like of the dried material, and homogeneously calcine the dried material, the dried material is calcined preferably while the calcining tube is being rotated with its longitudinal direction as its axis. The rotation rate of the calcining tube is preferably 0.1 rpm or higher and 30 rpm or lower, more preferably 0.5 rpm or higher and 20 rpm or lower, and still more preferably 1.0 rpm or higher and 10 rpm or lower.

In the calcination of the dried material, from the viewpoint of making an obtained composite oxide to be in a favorable redox state, improving the performance of the composite oxide, and the like, with respect to the heating temperature of the dried material, it is preferable that heating be started from a temperature lower than 400° C. and be carried out continuously or stepwise up to a temperature in the range of 550° C. or higher and 800° C. or lower.

The calcination atmosphere may be in an air atmosphere or under an air circulation, but from the viewpoint of easily regulating the composite oxide in a favorable redox state, and the like, it is preferable that at least a part of the dried material be calcined under the circulation of an inert gas, such as nitrogen, containing substantially no oxygen.

In the case of carrying out the calcination by a batch system, from the viewpoint of regulating in a favorable redox state, the feed volume of the inert gas is, per 1 kg of the dried material, preferably 50 NL/hr or larger, more preferably 50 NL/hr or larger and 5,000 NL/hr or smaller, and still more preferably 50 NL/hr or larger and 3,000 NL/hr or smaller. Here, "NL" means the standard temperature and pressure condition, that is, a volume (L) measured at 0° C. and 1 atm.

In the case of carrying out the calcination in a continuous system, from the viewpoint of regulating in a favorable redox state, the feed volume of the inert gas is, per 1 kg of the dried material, preferably 50 NL/hr or larger, more preferably 50 NL/hr or larger and 5,000 NL/hr or smaller, and still more preferably 50 NL/hr or larger and 3,000 NL/hr or smaller. At this time, the contact form of the inert gas with the dried material may be countercurrent contact or concurrent contact, but in consideration of gas components evolved from the dried material and air possibly mingling in a minute amount in the dried material, the countercurrent contact is preferable.

The dried material may contain, besides moisture, ammoniums, organic acids, inorganic acids and the like.

In the case of calcining the dried material under the circulation of an inert gas containing substantially no oxygen, when the dried material evaporates, decomposes and otherwise, the constituent elements of a composite oxide contained therein are reduced. In the case where the constituent elements of the composite oxide contained in the dried material have their nearly highest oxidation numbers, in order to make the reduction ratio of the composite oxide in a desired range, it suffices if reduction only is carried out in the step (3), which is industrially simple.

[Step (4): Impregnation Step]

The step (4) of the present embodiment is a step of impregnating the composite oxide obtained in the step (3) with a solution (impregnating solution) containing at least one specific element selected from the group consisting of tungsten, molybdenum, tellurium, niobium, vanadium, boron, bismuth, manganese, iron, antimony, phosphorus and rare earth elements to thereby obtain an impregnated composite oxide (hereinafter, referred to also as "impregnated composite oxide"). Then, at least one of the step (4) and the step (5) of drying is a step of impregnating the composite oxide or drying the impregnated composite oxide while stirring by a stirring power per unit composite oxide volume given by the following formula (2). That is, in the case where the step (5) is not a step meeting this requirement, the step (4) is a step meeting this requirement. Further both the step (4) and the step (5) may be steps meeting this requirement.

$$Pv\ (kW/m^3) = P\ (kW)/V\ (m^3) \qquad (2)$$

In the formula (2), Pv represents a stirring power ($kW/m^3$) per unit composite oxide volume; P represents an electric power (kW) used in the stirring time; and V represents a volume ($m^3$) of the composite oxide packed in a stirring apparatus. Pv is 0.001≤Pv≤300. The impregnating solution in the step (4) can be prepared from a specific raw material.

The impregnating solution is a solution containing at least one specific element selected from the group consisting of tungsten, molybdenum, tellurium, niobium, vanadium, boron, bismuth, manganese, iron, antimony, phosphorus and rare earth elements. These specific elements are preferably tungsten, niobium, molybdenum, bismuth, manganese and tellurium; and cerium and yttrium of rare earth elements, and more preferably tungsten, molybdenum, antimony, tellurium and cerium. The kind of the specific element is not especially limited, and it is preferable that one or more of the specific elements be suitably selected. The impregnating solution can be prepared by mixing the following raw material.

Examples of raw materials of tungsten include: though limited to the following, powdery raw materials of salts of tungsten such as ammonium salt, nitrate salt, carboxylate salt, carboxylic acid ammonium salt, peroxocarboxylate salt, peroxocarboxylic acid ammonium salt, haloganated ammonium salt, halide, acetylacetonate, alkoxide, triphenylated substance, polyoxometalate and polyoxometalate ammonium salt; powdery raw materials of tungsten oxide, ammonium paratungstate, silicotungstic acid, silicotungstomolybdic acid, silicovanadotungstic acid and the like; and an ammonium metatungstate aqueous solution and tungsten oxide sol.

Examples of raw materials of molybdenum include, though limited to the following, ammonium heptamolybdate, molybdenum trioxide, phosphomolybdic acid, silicomolybdic acid, and molybdenum pentachloride.

Examples of raw materials of tellurium include, though limited to the following, oxide, hydride, halide, sulfide, carboxylate salt, and various types of complex salt.

Examples of raw materials of niobium include, though limited to the following, niobic acid, inorganic acid salt of niobium and organic acid salt of niobium.

Examples of raw materials of vanadium include, though limited to the following, ammonium metavanadate, vanadium pentaoxide and vanadium chloride.

Examples of raw materials of boron include, though limited to the following, oxide, sulfide, chloride, acid salt, perchlorate salt, carbonate salt, sulfate salt, carboxylate salt, and various types of complex salt.

Examples of raw materials of bismuth include, though limited to the following, oxide, nitrate salt, sulfate salt, halide, chloride, oxyhalide, triphenylated substance, bismuth molybdate, and various types of complex salt.

Examples of raw materials of manganese include, though limited to the following, hydride, oxide, permanganate salt, sulfate salt, nitrate salt, chloride, thiocyanate salt, acetate salt, phosphate salt, carbonate salt, halide, and various types of complex salt.

Examples of raw materials of iron include, though limited to the following, oxide, sulfide, chloride, perchlorate salt, carbonate salt, sulfate salt, carboxylate salt, and various types of complex salt.

Examples of raw materials of antimony include, though limited to the following, oxide, sulfide, chloride, nitrate salt, perchlorate salt, carbonate salt, sulfate salt, carboxylate salt, tartrate salt, and various types of complex salt.

Examples of raw materials of phosphorus include, though limited to the following, oxide, sulfide, chloride, nitrate salt, perchlorate salt, carbonate salt, sulfate salt, carboxylate salt, and various types of complex salt.

Examples of rare earth elements include raw materials of cerium and raw materials of yttrium. Then, the cerium raw material is not especially limited, but includes oxide, sulfide, chloride, nitrate salt, perchlorate salt, carbonate salt, sulfate salt, carboxylate salt, and various types of complex salt.

These raw materials may be used singly or may be used in a combination of a plurality of the raw materials.

As the impregnating solution, an aqueous solution containing the specific element or a dispersion in which a compound containing the specific element is dispersed in water or a solvent can be used by regulating pH according to needs. The solvent for dispersing the compound include solvents such as water, acetone, methanol and ethanol, but in consideration of easiness of handling, water is preferable.

In the step (4), the pH of the impregnating solution is not especially limited, but is preferably 0.5 or higher and 12.0 or lower, more preferably 2.0 or higher and 7.0 or lower, and still more preferably 3.0 or higher and 6.0 or lower.

A pH regulator is not especially limited, but in the case of regulating to an acidity, nitric acid is preferable; and in the case of regulating to a neutrality or basicity, ammonia is preferable.

The content of the specific element in the impregnating solution is, based on the mass of the impregnating solution, preferably 0.01 mol/kg or higher and 2.0 mol/kg or lower, more preferably 0.05 mol/kg or higher and 1.5 mol/kg or lower, and still more preferably 0.1 mol/kg or higher and 1.0 mol/kg or lower. The content of 0.01 mol/kg or higher is an amount enough to modify the composite oxide; and the content of 2.0 mol/kg or lower tends to be able to suppress the ion exchange by an excessive specific element.

In the step (4), the volume of the impregnating solution is, based on the pore volume of the composite oxide, preferably 0.1 time or larger and 3.0 times or smaller, more preferably 0.3 time or larger and 2.5 times or smaller, and still more preferably 0.5 time or larger and 2.0 times or smaller. The volume of the impregnating solution of 0.1 time or larger tends to be able to disperse the specific element homogeneously in the composite oxide; and the volume the impregnating solution of 3.0 times or smaller tends to be able to suppress the dissolving-out of metal elements in the composite oxide into the impregnating solution. For example, in the case where 100 kg of the composite oxide of 1.000 g/cc in specific gravity and 0.2 cc/g in pore volume is impregnated, the volume of the impregnating solution is preferably 2.0 L or larger and 60 L or smaller, more preferably 6.0 L or larger and 50 L or smaller, and still more preferably 10 L or larger and 40 L or smaller.

As a method of measuring the pore distribution of the catalyst, a gas adsorption method, a mercury penetration method and the like are known, but the value differs depending on the methods. The value of the pore distribution in the present embodiment is that determined by a mercury penetration method (using a Pore Master GT, manufactured by Quantachrome Instruments). The mercury penetration method used here is a method of measuring, by introducing mercury under pressure into the catalyst particle interior, the distribution of pore diameters from the relation between the pressure and the penetrating volume at this time, and gives, as primary data, a cumulative curve of corresponding pore volumes vs. pore diameters calculated by assuming the shape of the pores to be cylindrical. Plots of values obtained by primarily differentiating the cumulative curve of the pore volume based on the pore diameter vs. corresponding pore diameters are usually called a pore distribution. In detail, 0.4 to 0.6 g of a sample (catalyst) is put in a dilatometer, which is then degassed down to 6.67 Pa or lower by a vacuum pump; thereafter, mercury is injected; then, the dilatometer is loaded on an autoclave; while the pressure is gradually applied from normal pressure up to 413 MPa, the decrease in the mercury liquid surface is traced and the pore distribution is measured from the pressures and the changes (volumes of mercury penetrated into catalyst pores) in the mercury liquid surface.

The liquid temperature of the impregnating solution is not especially limited, but is preferably 50° C. or lower, and more preferably 40° C. or lower. The liquid temperature of 50° C. or lower tends to be able to suppress the evaporation of the solvent during impregnation and improve the dispersibility of the specific element.

A technique for stirring the composite oxide and the impregnating solution is not especially limited, but includes a technique in which while the composite oxide is being stirred, the impregnating solution is dropped and added on the center of the composite oxide to thereby disperse the impregnating solution in the whole, and a technique in which without the composite oxide being stirred, the impregnating solution is sprayed and added on the whole to thereby disperse the impregnating solution in the whole; and from the viewpoint of homogeneously dispersing the impregnating solution in the composite oxide, preferable is the technique in which while the composite oxide is being stirred, the impregnating solution is sprayed and added on the whole. Another stirring technique includes also a technique of adding little by little the composite oxide to the impregnating solution, but from the viewpoint of reducing unevenness of dispersion of the impregnating solution in the composite oxide, and preventing deposition of the composite oxide on an inner wall of a stirring apparatus, preferable is a technique of adding the impregnating solution to the composite oxide to mix the both.

Examples of apparatuses to stir the composite oxide and the impregnating solution include an apparatus in which a rotating shaft and a rotating vane affixed thereto are installed in a lower part or an upper part of a tank, and stirring is carried out by a swirling flow by rotating the vane, and an apparatus in which the whole in a tank is stirred by rotating the whole of the tank. The former is better in the point that the dispersibility of the impregnating solution into the composite oxide is good, but the technique may suitably be selected according to the abrasion resistance and the specific gravity of the composite oxide, the specific gravity of the impregnating solution, and the like. The rotary vane is not especially limited as long as being capable of homogeneously stirring the composite oxide, but propeller-type ones and paddle-type ones can be used. Further the material for the stirring apparatus is not especially limited, but the one of, for example, SUS, glass, ceramic or a plastic such as Teflon®, or a composite material thereof can be used.

The stirring power (Pv) per unit composite oxide volume when the composite oxide and the impregnating solution are mixed is preferably 0.001 kw/m³ or higher and 300 kW/m³ or lower, more preferably 0.005 kw/m³ or higher and 280 kW/m³ or lower, and still more preferably 0.01 kw/m³ or higher and 260 kW/m³ or lower. That is, also in the step (4), the stirring power is preferably a stirring power per unit composite oxide volume given by the formula (2) described later. The Pv can be determined by dividing a working electric power (P) of a motor to be used for the stirring by a volume of the composite oxide to be subjected to an impregnation treatment. When the Pv is 0.001 kW/m³ or higher, because the stirring in the step (4) is carried out sufficiently, the yield of an unsaturated nitrile tends to be able to increase; and when the Pv is 300 kW/m³ or lower, the breakage of the catalyst tends to be able to be reduced.

In conventional production methods of the catalyst, when the composite oxide and the impregnating solution are charged and stirred in a stirring apparatus installed with a rotary vane in its tank lower part, and the volume of the composite oxide is gradually increased with the electric power being held constant, the load on the rotary vane increases correspondingly to the increase of the volume of the composite oxide. Since the electric power is constant despite that the load has increased, the rotation frequency of the rotary vane decreases along with the increase in the load and the degree of mixing of the composite oxide decreases. Conversely, when the volume of the composite oxide is gradually reduced with the electric power being held constant, the load of the rotary vane decreases. Since the electric power is constant despite that the load decreases, the rotation frequency of the rotary vane gradually increases, and consequently, it is presumed that forces of collision and forces of rubbing of the rotary vane with the composite oxide increase and the phenomenon of catalyst breakage is caused (causes, however, are not limited thereto). By contrast, in the method for producing a catalyst of the present embodiment, by regulating the electric power correspondingly to the volume of the composite oxide and making the electric power in a certain range, the mixed state of the composite oxide with the impregnating solution is made good, and breakage of the composite oxide itself can be suppressed. The volume of the composite oxide can be determined by the following formula.

Volume of the composite oxide (L)=a mass of the composite oxide (kg)/a bulk specific gravity (kg/L)

A method of measuring the bulk specific gravity (kg/L) involves preparing a vessel having a known volume, and first measuring the mass of the vessel alone. After the measurement, the vessel is taken off the balance and the composite oxide is packed in the vessel. At this time, the composite oxide overflows the measuring cylinder when the packing is stopped. Thereafter, the composite oxide bulging out from the upper part of the vessel is removed and leveled by a glass rod or the like; then, the composite oxide adhered on the circumference of the vessel is brushed off by a brush or the like; and thereafter, the mass is measured. The bulk specific gravity was determined by the following formula from the vessel masses before and after the packing of the composite oxide.

Bulk specific gravity (kg/L)=(the vessel mass (kg) after packing of the composite oxide−the empty vessel mass (kg))/the volume of the vessel (L)

The industrial catalyst is required to be produced in a mass production, and the amount of the composite oxide to be mixed at one time is preferably at least 10 kg or more, more preferably 30 kg or more, and still more preferably 50 kg or more. It is as described above that when a large amount of the catalyst is produced, there may possibly arise problems such as generation of breakage in the catalyst and the deterioration of the dispersibility of the specific element into the composite oxide. In the step (4) of the present embodiment, however, by setting the stirring power (Pv) given by the above-mentioned formula (2) at 0.001 kW/m³ or higher and 300 kW/m³ or lower, both the prevention of breakage of the catalyst and the good dispersibility of the specific element are simultaneously satisfied and then, a large amount of an impregnated catalyst can be produced at one time. The production of the catalyst may be carried out in a scale exceeding 100 kg, or may be carried out in scales exceeding 500 kg and 1,000 kg. Thereby, unevenness of the solvent in the impregnation time can be eliminated and the specific element can be homogeneously dispersed in the composite oxide. Then, when the unevenness of the solvent occurs in the impregnation time, portions where the solvent is thick tends to be thick in the specific element and portions where the solvent is thin tends to be thin in the specific element.

In the step (4), the temperature of the composite oxide is preferably 50° C. or lower, more preferably 45° C. or lower, and still more preferably 40° C. or lower. The temperature of 50° C. or lower tends to be able to suppress complete transpiration of the solvent during the mixing of the impregnating solution and the composite oxide and improve the dispersibility of the specific element. A method of regulating the temperature of the composite oxide is not especially limited, but includes a method in which the stirring apparatus is made to have a jacket structure, and the temperature is regulated by passing cold water through the jacket, and a method in which air at normal temperature is introduced in the interior of the stirring apparatus and the temperature is regulated.

In the step (4), the stirring time (time from the initiation of mixing of the composite oxide and the impregnating solution until shifting to the drying) is preferably within 2 hours, and more preferably within 1.5 hours. The stirring time of within 2 hours tends to be able to suppress the ion exchange between the metal element in the composite oxide and the specific element due to the presence of the composite oxide and the specific element in the liquid phase.

When the composite oxide and the impregnating solution are mixed, in the case where the volume of the impregnating solution is large, in order to separate the composite oxide and the solvent of the impregnating solution, filtration may be carried out.

[Step (5): Second Drying Step]

The step (5) of the present embodiment is a step of drying the impregnated composite oxide (hereinafter, referred to also as "impregnated composite oxide") obtained in the step (4). Further at least one of the step (4) the step (5) is a step of impregnating the composite oxide or drying the impregnated composite oxide while stirring by a stirring power per unit composite oxide volume given by the following formula (2). That is, in the case where the step (4) is not a step meeting this requirement, the step (5) is a step meeting this requirement. Further both the step (4) and the step (5) may be steps meeting this requirement.

$$Pv \text{ (kW/m}^3\text{)} = P \text{ (kW)}/V \text{ (m}^3\text{)} \quad (2)$$

In the formula (2), Pv represents a stirring power (kW/m$^3$) per unit composite oxide volume; P represents an electric power (kW) used in the stirring time; and V represents a volume (m$^3$) of the composite oxide packed in the stirring apparatus. Pv is $0.001 \leq Pv \leq 300$.

The catalyst obtained by drying the impregnated composite oxide obtained in the step (4) exhibits a higher yield of an unsaturated nitrile when the catalyst is subjected to a gas-phase catalytic ammoxidation reaction of propane than when a catalyst obtained without impregnation is subjected thereto. The cause that the yield becomes high is unclear, but is presumed as follows (the causes, however, are not limited thereto). First, the metal element in the composite oxide is replaced by the specific element in the impregnating solution stronger in oxygen bonding strength than the metal element, and it thereby becomes difficult for lattice oxygen in the composite oxide utilized for a dehydrogenation reaction of propane to move. It is presumed that by using the composite oxide after being thus made as the catalyst, the complete decomposition of propane is suppressed and the yield of the unsaturated nitrile is improved. Further it is conceivable that the replacement reaction of the metal element in the composite oxide by the specific element in the impregnating solution includes a replacement reaction (1) occurring "during the impregnation" and a replacement reaction (2) of molybdenum caused "during the gas-phase ammoxidation reaction". Further it is conceivable that it is the replacement reaction (2) occurring during the gas-phase ammoxidation reaction that contributes to the complete decomposition of propane. The reason is because in the case where a catalyst not having been subjected to the step (4) and the catalyst of the present embodiment are simultaneously subjected to the ammoxidation reaction in separate reactors, although the yields of the unsaturated nitrile at the first day when the reaction is started are equal for both the catalysts, in the reaction using the catalyst of the present embodiment, it is confirmed that the yield tends to gradually increase. From this result, if the replacement reaction (1) contributed to the improvement in the yield of the unsaturated nitrile, a difference in the yields of the unsaturated nitrile should be observed from the early phase of the reaction. Hence, it is presumed that the replacement reaction contributing to the improvement in the yield of the unsaturated nitrile does not occur at least during the impregnation but occurs during the ammoxidation reaction. Further, even if there is the specific element incorporated in the composite oxide by the replacement reaction (1) before the ammoxidation reaction (for example, during the impregnation), this does not contribute to the improvement in the yield of the unsaturated nitrile. Therefore, if the replacement reaction (1) during the impregnation can be suppressed and the replacement reaction (2) during the ammoxidation reaction can be promoted, it conceivably leads also to the improvement in the yield of the unsaturated nitrile. Hence, examples of control methods for suppressing the replacement reaction (1) during the impregnation include a method in which making the stirring in the step (4) and/or the step (5) sufficient and suppressing unevenness of the solvent in the drying time to suppress partial presence in a high concentration of the specific element in the impregnating solution, and a method in which the control is carried out so that the composite oxide and the impregnating solution are not present in the liquid phase for a long time. Particularly controlling these is preferable in the case of large-scale production in which the replacement reaction (1) during the impregnation easily occurs; the dispersibility of the impregnating solution is poor; and a long time for drying is needed.

An apparatus for drying the impregnated composite oxide is not especially limited, but techniques employed therein include a technique in which after the composite oxide is mixed in a stirring apparatus, the composite oxide is heated and thereby dried in the same apparatus, and a technique in which after the composite oxide is stirred in a stirring apparatus, the composite oxide is transferred to a separate drying apparatus and heated and thereby dried. The former technique, since from mixing to drying can be completed by one apparatus, has an advantage of being capable of making the space for installing the facility small. The latter technique, since stirring and drying can be continuously repeated by carrying out the mixing and the drying in separate apparatuses, has an advantage of being capable of raising the productivity. When the impregnated composite oxide is dried in a stirring apparatus, as a method of fluidizing the impregnated composite oxide, stirring by a rotary vane is preferable, but the impregnated composite oxide may be fluidized by introduction of a gas, or rotation of a whole tank. The separate drying apparatus is not limited to the following, but examples thereof include continuous-type drying apparatuses such as kilns, and batch-type drying apparatuses. The continuous-type drying apparatuses such as kilns, since being capable of continuously drying, have an advantage of being capable of raising the productivity. On the other hand, the batch-type drying apparatuses have an advantage of being easily controlled. Further the material for the drying apparatuses is not especially limited, but for example, SUS, glass, ceramic, plastic such as Teflon, and composite materials thereof can be used.

In the step (5), the drying rate is preferably 0.5% by mass/hr or higher and 20% by mass/hr or lower, and more preferably 1.0% by mass/hr or higher and 15% by mass/hr or lower. Here, the drying rate is determined by the following formula (3).

Drying rate=(a water content before the drying treatment−a water content after the drying treatment)/a drying time (3)

With respect to the drying treatment, a time point when the operation of the apparatus is started is regarded as the start of the drying treatment. Further a time point when the water content becomes lower than 1.0% by mass is regarded as the finish of the drying treatment, and the time from the start to the finish of the drying treatment is regarded as a drying time. A technique of judging "a time point when the water content becomes lower than 1.0% by mass" is not especially limited, but one example involves that samplings for measuring the amounts of water contained are carried out at least one time in 1 hour and a sampling time point when the water content becomes lower than 1.0% by mass can be regarded as "a time point when the water content becomes lower than 1.0% by mass". The samplings are required to be carried out at least one time in 1 hour, but may be carried out at any intervals as long as being within 1 hour. The drying time in a predetermined drying condition is previously measured; and in the case where the drying is carried out under the condition, there is no need of sampling, and it is regarded that the drying treatment has finished at the time point when the previously measured time has passed. Further also in the case where the water content has become 0% by mass, the drying treatment is regarded as having been finished. Here, after the drying treatment is finished, the composite oxide is allowed to be further put under the drying condition.

In the step (5), when the drying rate is 0.5% by mass/hr or higher and 20% by mass/hr or lower while the impregnated composite oxide is being fluidized, it is likely that the performance of the obtained catalyst and the yield of acrylonitrile tend to be improved. The cause is unclear, but is presumed as follows (causes, however, are not limited thereto). With the drying rate of 0.5% by mass/hr or higher, the performance of the obtained catalyst tends to be improved, because the contact of the impregnating solution with the impregnated composite oxide at a temperature higher than normal temperature occurs in a short time, and then, the dissolving-out of metal elements from active crystals governing the performance as the catalyst in the impregnated composite oxide and the excessive replacement by the specific element in the impregnating solution are suppressed. Further when the drying rate is 20% by mass/hr or lower, due to that it is suppressed that the impregnating solution having entered pores in the impregnated composite oxide comes out on the surface of the composite oxide and then, the metal element in the impregnating solution is nonuniformly distributed on the surface of the impregnated composite oxide, the performance of the obtained catalyst tends to be improved. Further, due to that in the step (5), by drying the impregnated composite oxide while fluidizing it, unevenness in the drying state of the catalyst, which is liable to become a problem when a large amount of the catalyst is produced, is suppressed, the performance of the obtained catalyst tends to be improved.

The drying rate in the above-mentioned range is not especially limited, but for example, can be materialized by regulating the drying condition in the step (5), such as the temperature of the composite oxide, the pressure in the apparatus (hereinafter, referred to also as "in-tank pressure" or "apparatus internal pressure") and the gas flow volume made to flow in the apparatus interior.

In the step (5), the pressure in the apparatus is, in absolute pressure, preferably 20 kPa or higher and 110 kPa or lower, and more preferably 30 kPa or higher and 110 kPa or lower.

When the pressure in the apparatus is in the above range, the drying time can be shortened and it is presumably likely that the moisture having entered pores can be prevented from coming out on the surface of the impregnated composite oxide and then, it can be suppressed that the metal element in the impregnating solution is nonuniformly distributed.

In the step (5), the temperature of the composite oxide is preferably 30° C. or higher and 650° C. or lower, more preferably 40° C. or higher and 550° C. or lower, still more preferably 50° C. or higher and 500° C. or lower, and further still more preferably 60° C. or higher and 400° C. or lower. The temperature regulated in such a range tends to be able to dry the impregnated composite oxide quickly without deterioration of the impregnated composite oxide. The temperature of 30° C. or higher tends to be able to dry the impregnated composite oxide quickly; and the temperature of 650° C. or lower tends to be able to prevent the deterioration due to peroxidation of the impregnated composite oxide itself and the damage of the catalyst due to bumping. For the catalyst to be dried at a temperature exceeding 550° C., the drying is preferably carried out by circulating an inert gas such as nitrogen in order to avoid the deterioration due to peroxidation. A method of regulating the temperature of the composite oxide is not especially limited, but examples thereof include a method in which an apparatus to be used for drying is made to have a jacket structure, and hot water, steam or the like is passed through the jacket portion for warming, a method in which heated air or inert gas is introduced in the stirring apparatus interior for warming, and a method in which a rotating shaft is installed in the stirring apparatus interior and rotated for warming by frictional heat generated by its rotation. In consideration of the operability of the temperature regulation, preferable is the system which is made to have a jacket structure, through which hot water or steam is passed. Since moisture is much present in the early period in the drying treatment, the temperature of the composite oxide are never elevated exceeding the boiling point of water; however, establishing the drying condition so as to exceed the boiling point of water, since more heat per unit time is supplied, is effective on that the drying is quickly advanced. Here, since the water content sufficiently decreases just before the finish of the drying treatment, the temperature of the composite oxide may possibly be elevated exceeding the boiling point of water; so, an exact value of the above-mentioned "temperature of the composite oxide" can be acquired by checking the temperature just before the finish of the drying treatment.

In the case where in the step (5), the temperature is elevated to the above temperature range, the temperature-elevation pattern is not especially limited, and may be a constant-rate temperature-elevation one, or in an irregular-rate temperature-elevation one. Further in the course of the temperature-elevation, the temperature is allowed to be lowered or to be held at a certain temperature on the way. From the viewpoint of quickly drying the composite oxide without deteriorating it, it is preferable that heat be continuously supplied up to a target temperature. Further in the case where the drying treatment is finished and the temperature is lowered, the temperature-fall pattern is also not especially limited, but it is preferable that the temperature be continuously lowered down to nearly room temperature (for example, 25° C.)

In the step (5), the drying time is preferably 0.5 hour or longer and 50 hours or shorter, more preferably 1.0 hour or longer and 48 hours or shorter, and still more preferably 2.0 hours or longer and 36 hours or shorter. The drying time of 0.5 hour or longer tends to be able to provide a catalyst low in the water content and high in the performance. This is presumed that when the drying time is 0.5 hour or longer, the performance of the obtained catalyst is improved, because it is suppressed that the impregnating solution having entered pores in the impregnated composite oxide comes out on the surface of the impregnated composite oxide abruptly and then, the metal element in the impregnating solution is nonuniformly distributed on the surface of the impregnated composite oxide. Further with the drying time of 50 hours or shorter, it is likely that the catalyst can be produced in a good productivity. This is presumed that when the drying time is 50 hours or shorter, the contact of the impregnating solution with the impregnated composite oxide at a temperature higher than normal temperature occurs in a short time, and then, the dissolving-out of metal elements from active crystals governing the performance as the catalyst in the impregnated composite oxide, and the excessive replacement by the specific element in the impregnating solution are suppressed. Here, the drying time in the case where the drying is carried out in a continuous-type kiln or the like is, for 90% by mass or more of the total amount of the catalyst obtained, preferably 0.5 hour or longer and 50 hours or shorter, more preferably 1.0 hour or longer and 48 hours or shorter, and still more preferably 2.0 hours or longer and 36 hours or shorter.

In the case where in the step (5), the impregnated composite oxide is fluidized by introducing a gas, the kind of the gas made to flow in the apparatus interior is not especially limited, but in the case of industrial utilization, air is preferable because of its simplicity. The flow volume of the gas may suitably be regulated while the condition of the apparatus interior is being grasped.

In the step (5), the stirring power (Pv) per unit composite oxide volume determined from the above-mentioned formula (2) is preferably 0.001 kw/m$^3$ or higher and 300 kW/m$^3$ or lower, more preferably 0.005 kw/m$^3$ or higher and 280 kW/m$^3$ or lower, and still more preferably 0.01 kw/m$^3$ or higher and 260 kW/m$^3$ or lower. That is, also in the step (5), the stirring power can be made to be a stirring power per unit composite oxide volume given by the formula (2). The Pv can be determined by dividing an electric power consumed (P) by a driving section of a motor to be used for the stirring by a volume of the composite oxide to be impregnated. When the Pv is made to be 0.001 kW/m$^3$ or higher, because the stirring in the step (5) is carried out sufficiently to eliminate the unevenness of the solvent in the drying time and the yield of an unsaturated nitrile tends to be able to increase; and when the Pv is 300 kW/m$^3$ or lower, breakage of the catalyst can be reduced.

[Catalyst]

The catalyst of the present embodiment can be obtained by the method for producing the catalyst of the present embodiment. By using the catalyst of the present embodiment for a gas-phase catalytic ammoxidation reaction of propane, an unsaturated nitrile can be obtained in a high yield from propane.

The solvent content of the catalyst is preferably 0.01% by mass or higher and 5.0% by mass or lower, more preferably 0.05% by mass or higher and 4.0% by mass or lower, and still more preferably 0.1% by mass or higher and 3.0% by mass or lower. The solvent content of 0.01% by mass or higher tends to make achievement even if a drying condition mild for the composite oxide is selected; and the solvent content of 5.0% by mass or lower tends to be able to suppress dissolving-out of metal elements in the catalyst into the remaining solvent when the obtained catalyst is stored for a long period. The solvent content can be determined from the weight loss ratio before and after the catalyst is put in an electric oven at 100° C. for 12 hours, but the method is not limited thereto, and it suffices if the method is one capable of measuring the amount of solvent adsorbed on the catalyst.

In order to quantitatively check breakage of the catalyst, the same method as in an abrasion resistance test can be used. This is a test method in which a high-speed air is dashed against a powder and broken particle pieces are trapped, and the abrasion of the powder is quantitatively checked by using the mass of the trapped particle pieces. Specifically, a SUS tube of 2 inches in diameter and 1,000 mm in length is vertically installed; a three-holed plate having three holes of 1 mm in diameter is fixed on the lower part of the SUS tube; and 50 g of the catalyst is packed in the SUS tube and on the upper part of the three-holed plate. Thereafter, a cone of 4 inches in diameter and 1,000 mm in length is attached on the upper part of the SUS tube; a filter whose mass is previously measured is attached in the upper part of the cone in order to trap the flying catalyst; and air is made to flow in from the three-holed plate on the lower part of the SUS tube at 700 L/min. The filter is removed after 20 hours, and the amount of breakage can quantitatively be checked from a difference in filter mass between before and after the treatment.

In the catalyst, it is preferable that the elemental ratio of the specific element to molybdenum of the composite oxide represented by the above formula (1) be 0.0001 or higher and 0.50 or lower. The elemental ratio of the specific element is an elemental ratio of the specific element incorporated in the composite oxide by the impregnation, and is an elemental ratio (specific element/Mo) per one element of molybdenum in the composite oxide. The quantitative determination of the specific element incorporated in the composite oxide in the step (4) can be determined by measuring a composition of the catalyst and a composition of the composite oxide by an X-ray fluorescence analysis and by using the following formula.

Elemental ratio of the specific element=(a compositional ratio of the specific element in the catalyst)−(a compositional ratio of the specific element in the composite oxide)

The elemental ratio (specific element/Mo) is preferably 0.0001 or higher and 0.5 or lower, more preferably 0.0005 or higher and 0.3 or lower, and still more preferably 0.001 or higher and 0.1 or lower. When the elemental ratio (specific element/Mo) is 0.0001 or higher, it is likely that the composite oxide can sufficiently be modified and when the composite oxide is subjected to an ammoxidation reaction, the yield is improved. Further the elemental ratio (specific element/Mo) of 0.5 or lower tends to be able to suppress the ion exchange between the excessive specific element and the metal element in the composite oxide.

[Method for Producing an Unsaturated Nitrile]

A method for producing an unsaturated nitrile of the present embodiment is a method for producing an unsaturated nitrile by a gas-phase catalytic ammoxidation reaction of propane, and comprises a contact step of bringing the catalyst obtained by the production method of the catalyst of the present embodiment into contact with propane. As a specific example, there will be described a method for producing a corresponding unsaturated nitrile by bringing a raw material gas containing propane, ammonia and oxygen into contact with the catalyst accommodated in a reactor to thereby carry out a gas-phase catalytic ammoxidation reaction of propane.

Propane and ammonia are not limited to high-purity ones, and there can be used propane containing 5.0% by volume or smaller of impurities such as ethane, ethylene, n-butane and isobutane; ammonia containing 1.0% by volume or smaller of impurities such as water; and an industrial-grade propane gas and ammonia gas.

A raw material gas containing oxygen is not especially limited, but examples thereof include air, air enriched with oxygen, pure oxygen; and these gases diluted with an inert gas such as helium, argon, carbon dioxide or nitrogen, or steam. Among these, in the case of the use in an industrial scale, use of air is preferable because of simplicity.

Examples of the reaction form include reaction forms of static bed, fluidized bed and moving bed, but from the viewpoint of heat removal of a reactor, the reaction form of fluidized bed is preferable.

The reaction temperature is not especially limited, but is preferably 350° C. or higher and 500° C. or lower, and more preferably 380° or higher and 470° C. or lower. When the reaction temperature is 350° C. or higher, it is likely that an ammoxidation reaction of propane can be advanced at a practical rate; and when being 500° C. or lower, it is likely that the decomposition of a target product can be suppressed.

A lower reaction pressure is likely to make good the selectivity of an unsaturated nitrile, and the reaction pressure is preferably $0.3 \times 10^{-5}$ Pa or higher and $5.0 \times 10^{-5}$ Pa or lower, and more preferably $0.5 \times 10^{-5}$ Pa or higher and $3.0 \times 10^{-5}$ Pa or lower.

The reaction system may be of a recycle type in which an unreacted raw material gas is recovered and again fed to a reactor, or may be of a once-through type in which the recycle of the raw material is not carried out, but a preferable compositional ratio of a raw material gas differs depending on the reaction system. For example, in the case of the reaction by the once-through type, since the conversion ratio of propane is required to be made high, the molar ratio (oxygen/propane) of oxygen to propane is preferably 0.5 or higher and 4.5 or lower, and more preferably 1.0 or higher and 4.0 or lower, and still more preferably 1.5 or higher and 3.5 or lower. On the other hand, in the case of recycling unreacted propane, in order to make high the selectivity of a corresponding unsaturated nitrile, since a condition that the conversion ratio of propane is suppressed low is preferable, the molar ratio (oxygen/propane) is preferably 0.2 or higher and 3.5 or lower, more preferably 0.6 or higher and 3.0 or lower, and still more preferably 1.0 or higher and 2.5 or lower. However, since the compositional ratio of the raw material gas may affect the outlet-port oxygen concentration, for either reaction system, it is preferable that the compositional ratio be determined by concurrently taking into consideration that the outlet-port oxygen concentration falls into a desired range.

According to the production method of the catalyst of the present embodiment, there can be provided an unsaturated nitrile in a high yield from propane and can be produced the catalyst which exhibits only a low breakage ratio in a large amount.

EXAMPLES

Hereinafter, the present embodiment will be described in more detail by way of specific Examples and Comparative Examples, but the present embodiment is not any more limited to these Examples and Comparative Examples without departing from its gist. Evaluations carried out in Examples and Comparative Examples described later were made by being measured by the following methods.

(Evaluation) Yield

In Examples and Comparative Examples, the yield (indicated as "Yield of AN", in Table 1) of acrylonitrile (hereinafter, AN) was determined as follows. The molar number of AN produced was measured by previously taking a calibration curve by a measurement using gas chromatography (GC) of AN gas having an already-known concentration, and thereafter, quantitatively injecting a gas produced by an ammoxidation reaction into GC. The yield of AN was calculated based on the following formula from the "molar number of AN produced" acquired by the measurement. The results are shown in Table 1.

Yield of AN (%)=(a molar number of AN produced)/(a molar number of propane fed)×100

Example 1

(Step (1): Preparation Step)

451.3 kg of ammonium heptamolybdate [$(NH_4)_6Mo_7O_{24}.4H_2O$], 54.7 kg of ammonium metavanadate [$NH_4VO_3$], 78.0 kg of biantimony trioxide [$Sb_2O_3$] and 8.9 kg of cerium nitrate hexahydrate [$Ce(NO_3)_3.6H_2O$] were added to 2,800 kg of water, and heated at 95° C. for 1 hour under stirring to thereby obtain an aqueous raw material liquid (I).

A niobium-mixed liquid was prepared by the following method. 229.5 kg of niobic acid containing 79.8% by mass in terms of $Nb_2O_5$ and 789.9 kg of oxalic acid dihydrate [$H_2C_2O_4.2H_2O$] were mixed in 10 kg of water. The molar ratio of the charged oxalic acid/niobium was 5.0, and the charged niobium concentration was 0.50 (mol-Nb/kg-liquid). The liquid was heated and stirred at 95° C. for 2 hours to thereby obtain a mixed liquid in which niobium was dissolved. The mixed liquid was allowed to stand still, and cooled with ice; thereafter, the solid was filtered off by suction filtration to thereby obtain a homogeneous niobium-mixed liquid. The molar ratio of oxalic acid/niobium of the niobium-mixed liquid was 2.68 by the following analysis.

10 g of the niobium-mixed liquid was precisely weighed in a crucible, dried at 95° C. for one night, and thereafter heat-treated at 600° C. for 1 hour to thereby obtain 0.7895 g of $Nb_2O_5$. From this result, the niobium concentration was 0.594 (mol-Nb/kg-liquid). 3 g of the niobium-mixed liquid was precisely weighed in a 300-mL glass beaker; 200 mL of hot water at about 80° C., and then, 10 mL of a 1:1 sulfuric acid were added. The obtained mixed liquid was titrated, while being held at a liquid temperature of 70° C. on a hot stirrer under stirring, by using a ¼N $KMnO_4$. A point where a faint pinkish color due to $KMnO_4$ continued for about 30 sec or longer was set as an end point. The concentration of oxalic acid was, as a result of a calculation by the following formula from the titrant volume, 1.592 (mol-oxalic acid/kg).

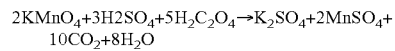

The obtained niobium-mixed liquid was used as a niobium raw material liquid ($B_0$) in the preparation of the following composite oxide.

52.0 kg of a hydrogen peroxide aqueous solution containing 30% by mass in terms of $H_2O_2$ was added to 361.8 kg of the niobium-mixed liquid ($B_0$), and stirred and mixed at room temperature for 10 min to thereby prepare an aqueous raw material liquid (II).

The obtained aqueous raw material liquid (I) was cooled down to 70° C.; thereafter, 791.1 kg of a silica sol containing 34.0% by mass in terms of $SiO_2$ was added; 90.9 kg of a hydrogen peroxide aqueous solution containing 30% by mass in terms of $H_2O_2$ was further added; and stirring at 55° C. was continued for 30 min. Then, the aqueous raw material liquid (II), 30.8 kg of an ammonium metatungstate aqueous solution containing 50% by mass in terms of $WO_3$, and 1,976.3 kg of a dispersion liquid in which a powdery silica was dispersed in water were added successively to thereby obtain an aqueous mixed liquid (III). The aqueous mixed liquid (III) was aged at 50° C. for 2 hours and 30 min from after the addition of the aqueous raw material liquid (II) to thereby obtain a slurry.

[Step (2): First Drying Step]

The obtained slurry was fed and dried in a centrifugal-type spray drier to thereby obtain a microspherical dried powder. The inlet port air temperature of the drier was 210° C., and the outlet port air temperature thereof was 120° C. The drying operation was repeated several times.

[Step (3): Calcination Step]

The obtained dried powder was packed in a SUS-made cylindrical calcining tube of 500 mm in inner diameter, 3,500 mm in length and 20 mm in wall thickness, and calcined at 680° C. for 2 hours under the circulation of a nitrogen gas at 600 NL/min with the tube being rotated to thereby obtain a composite oxide. The bulk specific gravity of the obtained composite oxide was measured and was 1.00; the pore volume thereof was 0.2 cc/g; and the catalyst composition was $Mo_{1.14}V_{0.21}Sb_{0.24}Nb_{0.103}W_{0.03}Ce_{0.009}$ (in Table, this catalyst composition is indicated as "A").

(Step (4): Impregnation Step)
(Preparation of an Impregnating Solution)

As the specific element impregnated in the composite oxide, tungsten was selected. 37.1 kg of a 50-mass % ammonium metatungstate aqueous solution was mixed in 162.9 kg of water to thereby obtain 200 kg as the impregnating solution. The temperature of the impregnating solution was 25° C. and the pH was 4.3.

(Mixing of the Composite Oxide with the Impregnating Solution)

Mixing of the obtained composite oxide with the obtained impregnating solution used a SUS-made stirring apparatus of 1,500 L in volume. The stirring method used a system in which the composite oxide and the impregnating solution were stirred and mixed by rotating a rotary vane installed in the lower tier in the apparatus, wherein the system used such a form that there was disposed a tilting paddle-type vane having four blades (rotary vane A) as the rotary vane in each of upper and lower two tiers thereof (with respect to a tilting paddle, see Chemical Engineering Handbook 7th revised ed. (Maruzen Publishing Co., Ltd.), 6th Chapter, "Stirring•Mixing" (in Japanese)). As a temperature-regulating method of the composite oxide packed in the apparatus, there was selected a system in which the temperature was regulated by passing cold water, hot water or steam through a jacket installed on the outside of the apparatus. As a technique of adding the impregnating solution, there was selected a system of adding the impregnating solution by spraying from the central upper part of the apparatus. 1,000 kg (1,000 L in volume) of the composite oxide was charged in the stirring apparatus; the rotary vane was operated and when the rotation frequency was raised until a time when the working electric power of a drive motor for the rotary vane became 50 kW, the rotation frequency of the rotary vane was 200 rpm. 200 kg of the impregnating solution was added over 5 min while the composite oxide was being stirred, and stirring was carried out further for 5 min. The temperature of the composite oxide was 20° C.

(Step (5): Second Drying Step)

The above apparatus having mixed the composite oxide and the impregnating solution was used as it was, and the composite oxide was dried with the working electric power of the motor for the rotary vane being made to be equal to that in the mixing time, to thereby obtain an impregnated catalyst. The pressure in the apparatus was made to be 50 kPa by using a vacuum pump simultaneously with the initiation of the drying, and the temperature in the tank in the drying time was regulated so as to become 80° C. by making hot water to flow through the jacket. Since no steam came to be generated from the impregnated catalyst after the lapse of 7.0 hours from the initiation of the drying, the hot water having been made to flow through the jacket was switched to cold water to cool the impregnated catalyst. The drying rate, the in-tank pressure, the drying time and the temperature of the composite oxide are shown in Table 1. The drying rate was determined by the following formula (3).

$$\text{Drying rate} = (\text{a water content before the drying treatment} - \text{a water content after the drying treatment})/\text{a drying time} \quad (3)$$

Here, the water content before the drying treatment was 15.12% by mass from 181.45 kg of water to 1,200 kg of the total amount of 1,000 kg of the composite oxide and 200 kg of the impregnating solution. Then, the water content after the drying treatment used a value of the following (physical property 1) water content, and the drying time was 7.0 hours. From these, the drying rate was 2.1% by mass/hr.

(Physical Property 1) Water Content

The water content of the obtained impregnated catalyst was measured as follows. 100.0045 g of the impregnated catalyst was charged in a SUS vessel, and dried in an electric oven at 100° C. for 12 hours. The resultant was taken out from the electric oven after the drying, and cooled to normal temperature; and the mass of the impregnated catalyst was measured and was 96.3633 g. The water content determined from a mass loss before and after the drying is shown in Table 1.

(Physical Property 2) Elemental Ratio of a Specific Element (Specific Element/Mo)

The elemental ratio of a specific element to Mo in the obtained composite oxide or impregnated catalyst was measured as follows. The compositional analysis of the composite oxide or impregnated catalyst was carried out. The compositional analysis used an X-ray fluorescence analyzer (trade name: "RIX1000" manufactured by Rigaku Corp.). The W/Mo ratio determined from the result of the compositional analysis is shown in Table 1.

(Physical Property 3) Breakage Ratio

The breakage ratio of the obtained impregnated catalyst was measured as follows. A SUS tube of 2 inches in diameter and 1,000 mm in length was vertically installed; a three-holed plate having three holes of 1 mm in diameter was fixed on the lower part of the SUS tube; and 50 g of the impregnated catalyst was packed therein. Thereafter, a cone of 4 inches in diameter and 1,000 mm in length was attached on the upper part of the SUS tube; a filter whose mass was previously measured was attached in the upper part of the cone in order to trap the flying impregnated catalyst; and air was made to flow in from the three-holed plate on the lower part of the SUS tube at 700 L/min; the filter was removed after 20 hours of the air flowing, and the mass of the filter was measured. By assuming that all of the impregnated catalyst recovered on the filter was broken impregnated catalysts, the ratio of the mass of the impregnated catalyst recovered on the filter to 50 g of the impregnated catalyst was defined as a breakage ratio (% by mass). The result is shown in Table 1.

(Ammoxidation Reaction of Propane)

600 kg of the obtained impregnated catalyst was packed in a SUS-made fluidized-bed reactor of 600 mm in inner diameter. Nozzles to feed a gas containing propane and ammonia through were installed vertically downward at the positions of 30 cm above from the catalyst-packed section bottom surface of the reactor. The installation positions (five positions in total) were made to be the center of the reactor and vertexes of a square of 340 mm in one side with the center of the square being on the center of the reactor. Nozzles to feed a gas containing oxygen through were installed vertically upward on the catalyst-packed section bottom surface of the reactor. The installation positions were made to be positions (five positions) superposed in the vertical direction on the nozzles to feed the gas containing propane and ammonia. For the heat removal of the reactor, there were installed four cooling coils to be used stationarily and two cooling coils for temperature fine control in the catalyst-concentrated layer. With the catalyst temperature being 445° C. and the reaction pressure being 40 kPa, propane and ammonia from the nozzles on the upper side and air from the nozzles on the lower side were fed in a molar ratio of propane:ammonia:oxygen=1:0.93:2.81 so that the contact time became 3.4 sec·g/cc; then, the oxygen concentration in a gas produced at the reactor outlet port indicated 3.1%. The reaction was continued for 2 weeks. The yield of AN after the two-week continuation is shown in Table 1.

Examples 2 to 5

Impregnated catalysts were produced and the ammoxidation reaction of propane was carried out under the same condition as in Example 1, except for so regulating the working electric power of the drive motor for the rotary vane that the Pv in the steps (4) and (5) became conditions indicated in Table 1, respectively. The results are shown in Table 1.

Example 6

An impregnated catalyst was produced and the ammoxidation reaction of propane was carried out under the same condition as in Example 1, except for changing the form (rotary van A) of the apparatus used for mixing and drying in the steps (4) and (5) to a form (rotary vane B) in which there was disposed a tilting paddle-type vane having two blades in each of upper and lower two tiers thereof, and using the resultant apparatus. The results are shown in Table 1.

Example 7

An impregnated catalyst was produced and the ammoxidation reaction of propane was carried out under the same condition as in Example 1, except for changing the apparatus used for mixing and drying in the steps (4) and (5) to an apparatus having a driving section of the rotary vane in the upper part of the apparatus and using the resultant apparatus. The results are shown in Table 1.

Example 8

An impregnated catalyst was produced and the ammoxidation reaction of propane was carried out under the same condition as in Example 1, except for that, in the step (4), as the specific element to be impregnated in the composite oxide, antimony was selected and 29.2 kg of a 30-mass % antimony sol aqueous solution was dispersed in 170.8 kg of water to thereby obtain 200 kg as the impregnating solution. The temperature of the impregnating solution in the step (4) was 25° C. and the pH was 4.6. The results are shown in Table 1.

Example 9

An impregnated catalyst was produced and the ammoxidation reaction of propane was carried out under the same condition as in Example 1, except for that, in the step (4), as the specific element to be impregnated in the composite oxide, cerium was selected and 0.9 kg of a 98-mass % cerium nitrate was mixed in 199.1 kg of water to thereby obtain 200 kg as the impregnating solution. The temperature of the impregnating solution in the step (4) was 25° C. and the pH was 3.8. The results are shown in Table 1.

Example 10

An impregnated catalyst was produced and the ammoxidation reaction of propane was carried out under the same condition as in Example 1, except for that, in the step (4), as the specific element to be impregnated in the composite oxide, tellurium was selected and 4.7 kg of a 99-mass % telluric acid was mixed in 195.3 kg of water to thereby obtain 200 kg as the impregnating solution. The temperature of the impregnating solution in the step (4) was 25° C. and the pH was 3.7. The results are shown in Table 1.

Example 11

An impregnated catalyst was produced and the ammoxidation reaction of propane was carried out under the same condition as in Example 1, except for that, in the step (4), as the specific element to be impregnated in the composite oxide, molybdenum was selected and 3.5 kg of a 99.3-mass % ammonium heptamolybdate was dispersed in 196.5 kg of water to thereby obtain 220 kg as the impregnating solution. The temperature of the impregnating solution in the step (4) was 25° C. and the pH was 5.5. The results are shown in Table 1.

Examples 12 to 17

Impregnated catalysts were produced and the ammoxidation reaction of propane was carried out under the same condition as in Example 1, except for so regulating the working electric power of the drive motor for the rotary vane that the Pv only in the step (5) became conditions indicated in Table 1, respectively. The results are shown in Table 1.

Examples 18 to 23

Impregnated catalysts were produced and the ammoxidation reaction of propane was carried out under the same condition as in Example 1, except for so regulating the working electric power of the drive motor for the rotary vane that the Pv only in the step (4) became conditions indicated in Table 1, respectively. The results are shown in Table 1.

Example 24

An impregnated catalyst was produced and the ammoxidation reaction of propane was carried out under the same condition as in Example 1, except for that: normal-pressure steam was made to flow through the jacket and regulated so that the temperature of the composite oxide in the drying time in the step (5) became 80° C.; after 7.0 hours of the drying, a part of the catalyst was extracted; the drying was continued also after the extraction of the catalyst; the water content of the part extracted of the catalyst was measured after 7.0 hours and was 0.23% by mass; after 1.0 hour, the temperature of the composite oxide rose to 100° C. due to heat by the normal-pressure steam and due to the frictional heat by stirring; the catalyst was sampled and the water content was measured and was 0.00% by mass; thereafter, the steam having been made to flow through the jacket was switched to a cold water to cool the impregnated catalyst; thus, the drying time became 8.0 hours in total. The results are shown in Table 1.

Examples 25 and 26

Impregnated catalysts were produced and the ammoxidation reaction of propane was carried out under the same condition as in Example 1, except for regulating the pressure in the apparatus in the step (5) by using a vacuum pump so that the pressure became 75 kPa and 101 kPa in absolute pressure, respectively, and finishing the drying after the lapse of 14 hours and 20 hours from the initiation of the drying, respectively. The results are shown in Table 1.

Example 27

[Step 1: Preparation Step]
53.1 kg of ammonium heptamolybdate [$(NH_4)_6Mo_7O_{24} \cdot 4H_2O$], 53.1 kg of ammonium metavanadate [$NH_4VO_3$], 119.3 kg of telluric acid [$Te(OH)_6$] and 8.6 kg of cerium nitrate hexahydrate [$Ce(NO_3)_3 \cdot 6H_2O$] were added to 2,717 kg of water, and stirred to thereby obtain an aqueous raw material liquid (I).

50.5 kg of a hydrogen peroxide aqueous solution containing 30% by mass in terms of $H_2O_2$ was added to 351.4 kg of the niobium-mixed liquid ($B_0$), and stirred and mixed at room temperature for 10 min to thereby prepare an aqueous raw material liquid (II).

791.1 kg of a silica sol containing 34.0% by mass in terms of $SiO_2$ was added to the obtained aqueous raw material liquid (I). Then, the aqueous raw material liquid (II), 29.9 kg of an ammonium metatungstate aqueous solution containing 50% by mass in terms of $WO_3$, and 1,976.3 kg of a dispersion liquid in which a powdery silica was dispersed in water were added successively to thereby obtain an aqueous mixed liquid (III). The aqueous mixed liquid (III) was aged at 50° C. for 2 hours and 30 min from after the addition of the aqueous raw material liquid (II) to thereby obtain a slurry.

[Step (2): First Drying Step]
The obtained slurry was fed and dried in a centrifugal-type spray drier to thereby obtain a microspherical dried powder. The inlet port air temperature of the drier was 210° C., and the outlet port air temperature thereof was 120° C. The drying operation was repeated several times.

[Step (3): Calcination Step]
The obtained dried powder was packed in a SUS-made cylindrical calcining tube of 500 mm in inner diameter, 3,500 mm in length and 20 mm in wall thickness, and calcined at 680° C. for 2 hours under the circulation of a nitrogen gas at 600 NL/min with the tube being rotated to thereby obtain a composite oxide. The bulk specific gravity of the obtained composite oxide was measured and was 1.00; the pore volume thereof was 0.2 cc/g; and the catalyst composition was $Mo_{1.14}V_{0.21}Te_{0.24}Nb_{0.103}W_{0.03}Ce_{0.009}$ (in Table, this catalyst composition is indicated as "B").

An impregnated catalyst was produced and the ammoxidation reaction of propane was carried out under the same condition as in Example 1, except for carrying out the operation in and after the step (4) instead of using the composite oxide obtained above. The results are shown in Table 1.

Examples 28 to 31

Impregnated catalysts were produced and the ammoxidation reaction of propane was carried out under the same condition as in Example 27, except for so regulating the working electric power of the drive motor for the rotary vane that the Pv in the steps (4) and (5) became conditions indicated in Table 1, respectively. The results are shown in Table 1.

Example 32

An impregnated catalyst was produced and the ammoxidation reaction of propane was carried out under the same condition as in Example 1, except for that, in the step (4), as the specific element to be impregnated in the composite oxide, tungsten was selected and 0.5 kg of a 50-mass % ammonium metatungstate aqueous solution was mixed in 199.5 kg of water to thereby obtain 200 kg as the impregnating solution. The temperature of the impregnating solution in the step (4) was 25° C. and the pH was 6.5. The results are shown in Table 1.

Example 33

An impregnated catalyst was produced and the ammoxidation reaction of propane was carried out under the same condition as in Example 1, except for that, in the step (4), as the specific element to be impregnated in the composite oxide, tungsten was selected and 10.7 kg of a 50-mass % ammonium metatungstate aqueous solution was mixed in 189.3 kg of water to thereby obtain 200 kg as the impregnating solution and the temperature of the impregnating solution in the step (4) was 25° C. and the pH was 4.5. The temperature of the impregnating solution in the step (4) was 25° C. and the pH was 4.5. The results are shown in Table 1.

Example 34

An impregnated catalyst was produced and the ammoxidation reaction of propane was carried out under the same condition as in Example 1, except for that, in the step (4), as the specific element to be impregnated in the composite oxide, tungsten was selected and 200.0 kg of a 50-mass % ammonium metatungstate aqueous solution was used as an impregnating solution. The results are shown in Table 1. The temperature of the impregnating solution in the step (4) was 25° C. and the pH was 3.35.

Example 35

An impregnated catalyst was produced and the ammoxidation reaction of propane was carried out under the same condition as in Example 1, except for that, in the step (4), as the specific element to be impregnated in the composite oxide, tungsten was selected, and 37.3 kg of a 50-mass % ammonium metatungstate aqueous solution was mixed in 159.7 kg of water, and thereafter, 3.0 kg of nitric acid was added to thereby obtain 200 kg as the impregnating solution. The temperature of the impregnating solution in the step (4) was 25° C. and the pH was 0.5. The results are shown in Table 1.

Example 36

In the step (4), as the specific element to be impregnated in the composite oxide, tungsten was selected, and 37.3 kg of a 50-mass % ammonium metatungstate aqueous solution was mixed in 161.1 kg of water, and thereafter, 1.6 kg of nitric acid was added to thereby obtain 120 kg as the impregnating solution. The temperature of the impregnating solution was 25° C. and the pH was 2.1. An impregnated catalyst was produced and the ammoxidation reaction of propane was carried out under the same condition as in Example 1, except for using the above impregnating solution. The results are shown in Table 1.

Example 37

An impregnated catalyst was produced and the ammoxidation reaction of propane was carried out under the same condition as in Example 1, except for that, in the step (4), as the specific element to be impregnated in the composite oxide, tungsten was selected, and 37.3 kg of a 50-mass % ammonium metatungstate aqueous solution was mixed in 161.7 kg of water, and thereafter, 1.0 kg of ammonia was added to thereby obtain 200 kg as the impregnating solution. The temperature of the impregnating solution in the step (4) was 25° C. and the pH was 10.2. The results are shown in Table 1.

Example 38

An impregnated catalyst was produced and the ammoxidation reaction of propane was carried out under the same condition as in Example 1, except for that, in the step (4), as the specific element to be impregnated in the composite oxide, tungsten was selected and 37.1 kg of a 50-mass % ammonium metatungstate aqueous solution was mixed in 2.9 kg of water to thereby obtain 40 kg as the impregnating solution. The temperature of the impregnating solution in the step (4) was 25° C. and the pH was 4.3. The results are shown in Table 1.

Example 39

An impregnated catalyst was produced and the ammoxidation reaction of propane was carried out under the same condition as in Example 1, except for that, in the step (4), as the specific element to be impregnated in the composite oxide, tungsten was selected, and 37.1 kg of a 50-mass % ammonium metatungstate aqueous solution was mixed in 462.9 kg of water to thereby obtain 500 kg as the impregnating solution. The temperature of the impregnating solution was 25° C. and the pH was 4.3. The results are shown in Table 1.

Example 40

An impregnated catalyst was produced and the ammoxidation reaction of propane was carried out under the same condition as in Example 1, except for that, in the step (4), as the specific element to be impregnated in the composite oxide, tungsten was selected, and 37.1 kg of a 50-mass % ammonium metatungstate aqueous solution was mixed in 662.9 kg of water to thereby obtain 700 kg as the impregnating solution. The temperature of the impregnating solution was 25° C. and the pH was 4.3. The results are shown in Table 1.

Comparative Example 1

In the step (4), no impregnating solution was used, and 1,000 kg (1,000 L in volume) of the composite oxide was charged in the stirring apparatus; the rotary vane was operated and when the rotation frequency was raised until a time when the working electric power of the drive motor for the rotary vane became 50 kW, the rotation frequency of the rotary vane was 200 rpm; and thereafter, the composite oxide was stirred for 10 min. An impregnated catalyst was produced and the ammoxidation reaction of propane was carried out under the same condition as in Example 1, except for not carrying out the step (5). The results are shown in Table 1.

Comparative Example 2

An impregnated catalyst was produced and the ammoxidation reaction of propane was carried out in the same manner as in Example 1, except for so regulating the working electric power of the drive motor for the rotary vane that the Pv in the steps (4) and (5) became 0.00077 (kW/m$^3$). The results are shown in Table 1.

Comparative Example 3

An impregnated catalyst was produced and the ammoxidation reaction of propane was carried out in the same manner as in Example 1, except for so regulating the working electric power of the drive motor for the rotary vane that the Pv in the steps (4) and (5) became 333 (kW/m$^3$). The results are shown in Table 1.

TABLE 1

| | Catalyst Composition Kind | Specific Element Kind | Impregnation Step Pv [kW/m$^3$] | Temperature of Composite Oxide [° C.] | Second Drying Step Pv [kW/m$^3$] | Drying Rate [% by mass/h] | In-Tank Pressure [kPa] |
|---|---|---|---|---|---|---|---|
| Example 1 | A | W | 50 | 20 | 50 | 2.1 | 50 |
| Example 2 | A | W | 21 | 20 | 21 | 2.1 | 50 |
| Example 3 | A | W | 19 | 20 | 19 | 2.1 | 50 |
| Example 4 | A | W | 0.05 | 20 | 0.05 | 1.0 | 50 |
| Example 5 | A | W | 250 | 20 | 250 | 3.0 | 50 |

TABLE 1-continued

| | | | | | | | |
|---|---|---|---|---|---|---|---|
| Example 6 | A | W | 50 | 20 | 50 | 2.1 | 50 |
| Example 7 | A | W | 50 | 20 | 50 | 2.1 | 50 |
| Example 8 | A | Sb | 50 | 20 | 50 | 2.1 | 50 |
| Example 9 | A | Ce | 50 | 20 | 50 | 2.1 | 50 |
| Example 10 | A | Te | 50 | 20 | 50 | 2.1 | 50 |
| Example 11 | A | Mo | 50 | 20 | 50 | 2.1 | 50 |
| Example 12 | A | W | 50 | 20 | 21 | 2.1 | 50 |
| Example 13 | A | W | 50 | 20 | 19 | 2.1 | 50 |
| Example 14 | A | W | 50 | 20 | 0.05 | 1.0 | 50 |
| Example 15 | A | W | 50 | 20 | 250 | 3.0 | 50 |
| Example 16 | A | W | 50 | 20 | 333 | 3.8 | 50 |
| Example 17 | A | W | 50 | 20 | 0.00077 | 0.6 | 50 |
| Example 18 | A | W | 21 | 20 | 50 | 2.1 | 50 |
| Example 19 | A | W | 19 | 20 | 50 | 2.1 | 50 |
| Example 20 | A | W | 0.05 | 20 | 50 | 2.1 | 50 |
| Example 21 | A | W | 250 | 45 | 50 | 2.1 | 50 |
| Example 22 | A | W | 333 | 50 | 50 | 2.1 | 50 |
| Example 23 | A | W | 0.00077 | 20 | 50 | 2.1 | 50 |
| Example 24 | A | W | 50 | 20 | 50 | 1.9 | 50 |
| Example 25 | A | W | 50 | 20 | 50 | 1.0 | 75 |
| Example 26 | A | W | 50 | 20 | 50 | 0.6 | 101 |
| Example 27 | B | W | 50 | 20 | 50 | 2.1 | 50 |
| Example 28 | B | W | 21 | 20 | 21 | 2.1 | 50 |
| Example 29 | B | W | 19 | 20 | 19 | 2.1 | 50 |
| Example 30 | B | W | 0.05 | 20 | 0.05 | 2.1 | 50 |
| Example 31 | B | W | 250 | 20 | 250 | 3.0 | 50 |
| Example 32 | A | W | 50 | 20 | 50 | 2.1 | 50 |
| Example 33 | A | W | 50 | 20 | 50 | 2.1 | 50 |
| Example 34 | A | W | 50 | 20 | 50 | 2.1 | 50 |
| Example 35 | A | W | 50 | 20 | 50 | 2.1 | 50 |
| Example 36 | A | W | 50 | 20 | 50 | 2.1 | 50 |
| Example 37 | A | W | 50 | 20 | 50 | 2.1 | 50 |
| Example 38 | A | W | 50 | 20 | 50 | 2.1 | 50 |
| Example 39 | A | W | 50 | 20 | 50 | 2.1 | 50 |
| Example 40 | A | W | 50 | 20 | 50 | 2.1 | 50 |
| Comparative Example 1 | A | — | 50 | 20 | — | — | — |
| Comparative Example 2 | A | W | 0.00077 | 20 | 0.00077 | 0.6 | 50 |
| Comparative Example 3 | A | W | 333 | 50 | 333 | 3.8 | 50 |

| | Second Drying Step | | Physical Properties of Catalyst | | | (Evaluation) |
|---|---|---|---|---|---|---|
| | Drying Time [Hour] | Temperature of Composite Oxide [° C.] | (Physical Property 1) Water Content [% by mass] | (Physical Property 2) Specific Element/Mo Ratio [—] | (Physical Property 3) Breakage Ratio [% by mass] | Yield [%] |
| Example 1 | 7 | 80 | 0.2 | 0.035 | 1.2 | 58.1 |
| Example 2 | 7 | 80 | 0.5 | 0.035 | 0.8 | 57.5 |
| Example 3 | 7 | 80 | 0.5 | 0.035 | 0.7 | 56.3 |
| Example 4 | 15 | 80 | 0.7 | 0.035 | 0.1 | 55.9 |
| Example 5 | 5 | 80 | 0.1 | 0.035 | 1.5 | 58.0 |
| Example 6 | 7 | 80 | 0.2 | 0.035 | 1.2 | 57.9 |
| Example 7 | 7 | 80 | 0.2 | 0.035 | 1.2 | 57.9 |
| Example 8 | 7 | 80 | 0.2 | 0.035 | 1.0 | 55.7 |
| Example 9 | 7 | 80 | 0.2 | 0.035 | 1.0 | 55.4 |
| Example 10 | 7 | 80 | 0.2 | 0.035 | 1.1 | 58.8 |
| Example 11 | 7 | 80 | 0.3 | 0.035 | 1.0 | 55.5 |
| Example 12 | 7 | 80 | 0.5 | 0.035 | 1.0 | 57.8 |
| Example 13 | 7 | 80 | 0.5 | 0.035 | 0.9 | 57.2 |
| Example 14 | 15 | 80 | 0.8 | 0.035 | 0.6 | 56.6 |
| Example 15 | 5 | 80 | 0.1 | 0.035 | 1.4 | 57.8 |
| Example 16 | 4 | 80 | 0.1 | 0.035 | 1.5 | 56.1 |
| Example 17 | 24 | 80 | 0.9 | 0.035 | 0.5 | 55.1 |
| Example 18 | 7 | 80 | 0.2 | 0.035 | 1.0 | 57.7 |
| Example 19 | 7 | 80 | 0.2 | 0.035 | 0.8 | 56.8 |
| Example 20 | 7 | 80 | 0.2 | 0.035 | 0.6 | 56.4 |
| Example 21 | 7 | 80 | 0.2 | 0.035 | 1.3 | 57.8 |
| Example 22 | 7 | 80 | 0.2 | 0.035 | 1.5 | 55.4 |
| Example 23 | 7 | 80 | 0.3 | 0.035 | 0.7 | 54.9 |
| Example 24 | 8 | 80 (100) | 0.0 | 0.035 | 1.4 | 57.7 |
| Example 25 | 14 | 80 | 0.3 | 0.035 | 1.8 | 57.2 |
| Example 26 | 24 | 80 | 0.8 | 0.035 | 2.1 | 56.4 |
| Example 27 | 7 | 80 | 0.2 | 0.035 | 1.2 | 58.4 |
| Example 28 | 7 | 80 | 0.5 | 0.035 | 0.8 | 57.7 |

TABLE 1-continued

| | | | | | | |
|---|---|---|---|---|---|---|
| Example 29 | 7 | 80 | 0.5 | 0.035 | 0.7 | 56.7 |
| Example 30 | 7 | 80 | 0.8 | 0.035 | 0.1 | 56.2 |
| Example 31 | 5 | 80 | 0.1 | 0.035 | 1.5 | 58.1 |
| Example 32 | 7 | 80 | 0.2 | 0.0005 | 0.9 | 56.0 |
| Example 33 | 7 | 80 | 0.2 | 0.01 | 1.0 | 57.4 |
| Example 34 | 7 | 80 | 0.2 | 0.25 | 1.1 | 56.5 |
| Example 35 | 7 | 80 | 0.2 | 0.035 | 1.0 | 54.8 |
| Example 36 | 7 | 80 | 0.2 | 0.035 | 0.9 | 57.0 |
| Example 37 | 7 | 80 | 0.2 | 0.035 | 1.0 | 55.2 |
| Example 38 | 2 | 80 | 0.6 | 0.035 | 0.9 | 58.0 |
| Example 39 | 16 | 80 | 0.3 | 0.035 | 0.9 | 57.6 |
| Example 40 | 19 | 80 | 0.5 | 0.035 | 1.1 | 54.7 |
| Comparative Example 1 | — | — | — | — | 0.7 | 53.5 |
| Comparative Example 2 | 24 | 80 | 0.8 | 0.035 | 0.1 | 52.5 |
| Comparative Example 3 | 4 | 80 | 0.1 | 0.035 | 5.3 | 53.9 |

The present application is based on Japanese Patent Application (Japanese Patent Application No. 2015-065054), filed in Japan Patent Office on Mar. 26, 2015, and Japanese Patent Application (Japanese Patent Application No. 2015-100183), filed in Japan Patent Office on May 15, 2015, and Japanese Patent Application (Japanese Patent Application No. 2015-154467), filed in Japan Patent Office on Aug. 4, 2015, the contents of which are hereby incorporated by reference.

The invention claimed is:

1. A method for producing a catalyst to be used for a gas-phase catalytic ammoxidation reaction of propane, the method comprising:
   a preparation step of dissolving or dispersing a raw material to thereby obtain a prepared raw material liquid;
   a first drying step of drying the prepared raw material liquid to thereby obtain a dried material;
   a calcination step of calcining the dried material to thereby obtain a composite oxide powder of a composite oxide represented by a formula (1);
   an impregnation step of impregnating the composite oxide powder by spraying to the composite oxide powder a solution containing at least one specific element selected from the group consisting of tungsten, molybdenum, tellurium, niobium, vanadium, boron, bismuth, manganese, iron, antimony, phosphorus and rare earth elements while stirring the composite oxide powder to thereby obtain an impregnated composite oxide powder; and
   a second drying step of drying the impregnated composite oxide powder while stirring the impregnated composite oxide powder,
   wherein the formula (1) is $Mo_1V_aNb_bA_cX_dZ_eO_n$ ... (1), where
   A represents at least one element selected from the group consisting of Sb and Te; X represents at least one element selected from the group consisting of W, Bi, Mn and Ti; and Z represents at least one element selected from the group consisting of La, Ce, Pr, Yb, Y, Sc, Sr and Ba; and a, b, c, d, e and n represent elemental ratios of the respective elements per one element of Mo and $0.01 \leq a \leq 1.00$, $0.01 \leq b \leq 1.00$, $0.01 \leq c \leq 1.00$, $0.00 \leq d \leq 1.00$ and $0.00 \leq e \leq 1.00$, and n is a value determined by the atomic valences of the constituent elements of the composite oxide, and
   wherein the impregnation step and the second drying step are carried out while stirring the composite oxide powder and the impregnated composite oxide powder, respectively, by a stirring power per unit composite oxide volume given by following formula (2):

$$Pv(kW/m^3) = P(kW)/V(m^3) \qquad (2),$$

where Pv represents a stirring power per unit composite oxide volume($kW/m^3$); P represents an electric power (kW) used in a stirring time; and V represents a volume ($m^3$) of the composite oxide powder or the impregnated composite oxide powder packed in a stirring apparatus; and Pv is $0.001 \leq Pv \leq 300$.

2. The method for producing the catalyst according to claim 1, wherein in the second drying step, the drying is carried out at a drying rate of 0.5% by mass/hr or higher and 20% by mass/hr or lower while the composite oxide powder is being fluidized.

3. The method for producing a catalyst according to claim 1, wherein in the catalyst, an elemental ratio of the specific element, which is impregnated to the composite oxide powder in the impregnation step, to the molybdenum (Mo) in the composite oxide represented by the formula (1) is 0.0001 or higher and 0.50 or lower.

4. The method for producing the catalyst according to claim 1, wherein in the second drying step, a pressure in an apparatus is 20 kPa or higher and 110 kPa or lower in absolute pressure.

5. The method for producing the catalyst according to claim 1, wherein in the second drying step, a drying time is 0.5 hour or longer and 50 hours or shorter.

6. The method for producing the catalyst according to claim 1, wherein in the second drying step, the composite oxide powder has a temperature of 30° C. or higher and 650° C. or lower.

7. The method for producing the catalyst according to claim 1, wherein in the impregnation step, a total volume amount of the solution sprayed to the composite oxide powder is 0.1 times or larger and 3.0 times or smaller of a pore volume of the composite oxide powder.

8. A method for producing an unsaturated nitrile by a gas-phase catalytic ammoxidation reaction of propane, the method comprising a contact step of bringing a catalyst obtained by the method for producing the catalyst according to claim 1 into contact with propane.

* * * * *